(12) United States Patent
Gudkov et al.

(10) Patent No.: US 8,318,724 B2
(45) Date of Patent: Nov. 27, 2012

(54) SMALL MOLECULE INHIBITORS OF MRP1 AND OTHER MULTIDRUG TRANSPORTERS

(75) Inventors: Andrei Gudkov, Gates Mills, OH (US); Michelle Haber, Coogee (AU); Murray Norris, Surry Hills (AU)

(73) Assignees: The Cleveland Clinic Foundation, Cleveland, OH (US); Children's Cancer Institute Australia for Medical Research, Randwick, New South Wales (AU)

( * ) Notice: Subject to any disclaimer, the term of this patent is extended or adjusted under 35 U.S.C. 154(b) by 902 days.

(21) Appl. No.: 11/579,779

(22) PCT Filed: May 13, 2005

(86) PCT No.: PCT/US2005/016832
§ 371 (c)(1),
(2), (4) Date: Nov. 7, 2006

(87) PCT Pub. No.: WO2005/113004
PCT Pub. Date: Dec. 1, 2005

(65) Prior Publication Data
US 2008/0032966 A1    Feb. 7, 2008

Related U.S. Application Data
(60) Provisional application No. 60/571,149, filed on May 14, 2004.

(51) Int. Cl.
*A61K 31/55* (2006.01)
(52) U.S. Cl. .................................................. 514/217.1
(58) Field of Classification Search ........................ None
See application file for complete search history.

(56) References Cited

U.S. PATENT DOCUMENTS

| | | | | |
|---|---|---|---|---|
| 5,639,756 | A * | 6/1997 | Anisimova et al. | 514/257 |
| 6,221,876 | B1 * | 4/2001 | Gruber et al. | 514/293 |
| 6,297,216 | B1 | 10/2001 | Sarkadi et al. | |
| 6,537,993 | B2 * | 3/2003 | Smith et al. | 514/249 |
| 2003/0073611 | A1 * | 4/2003 | Gudkov et al. | 514/1 |

OTHER PUBLICATIONS

Sarkadi et al. Interaction of bioactive hydrophobic peptides with the human multidrug transporter. FASEB J 8:766-770, 1994.*
Klappe K, Hinrichs JW, Kroesen BJ, Sietsma H, Kok JW. MRP1 and glucosylceramide are coordinately over expressed and enriched in rafts during multidrug resistance acquisition in colon cancer cells. Int J Cancer. 110(4):511-22, 2004.*
Rau S, Autschbach F, Riedel HD, Konig J, Kulaksiz H, Stiehl A, Riemann JF, Rost D. Expression of the multidrug resistance proteins MRP2 and MRP3 in human cholangiocellular carcinomas. Eur J Clin Invest. 38(2):134-42, 2008.*
Banker, G.S. et al, "Modern Pharmaceutics, 3ed.", Marcel Dekker, New York, 1996, p. 596.*
Wolff, Manfred E ((Burger's Medicinal Chemistry 5ed, Part I) John Wiley & Sons, 1995, pp. 975-977.*
Irwin (Curr Op Chem Biol 10:352-356, 2006).*
Han (Advances in Characterization of Pharmaceutical Hydrates. Trends in Bio/Pharmaceutical Industry, pp. 25-29. Mar. 2006).*
Vippagunta et al (Adv Drug Deliv Rev 48:3-26, 2001).*
Hennessy et al., "St. John's Wort Increases Expression of P-glycoprotein: Implications for Drug Interactions," *Br J Clin Pharmacol*, vol. 53, pp. 75-82 (2002).
International Search Resort in PCT/US2005/016832 dated Dec. 8, 2005.
Kondratov et al., "Small Molecules That Dramatically Alter Multidrug Resistance Phenotype by Modulating the Substrate Specificity of P-glycoprotein," *PNAS*, vol. 98, No. 24, pp. 14078-14083 (2001).
Kovarik et al., "Longitudinal Assessment of a P-glycoprotein-mediated Drug Interaction of Valspodar on Digoxin," *Clin Pharmacol Ther*, vol. 66, pp. 391-400 (1999).
Leonard, et al., "The Role of ABC Transporters in Clinical Practice," *The Oncologist*, vol. 8, pp. 411-424 (2003).
Mayer, et al., Full Blockage of Intestinal P-glycoprotein and Extensive Inhibition of Blood-brain Barrier P-glycoprotein by Oral Treatment of Mice with PSC833, *J. Clin. Invest.*, vol. 100, No. 10, pp. 2430-2436 (1997).
Wijnholds, "Drug Resistance Caused by Multidrug Resistance-Associated Proteins," *Novartis Foundation Symposium 243*, pp. 69-82 (2002).

* cited by examiner

*Primary Examiner* — Craig Ricci
(74) *Attorney, Agent, or Firm* — Marshall, Gerstein & Borun LLP

(57) ABSTRACT

A method of potentiating the activity of a therapeutic drug, like a chemotherapeutic drug or an antibiotic, in a cell or tissue, by inhibiting the efflux capability of a multidrug transporter are disclosed. The method is useful in the treatment of a cancer by sensitizing tumor cells to a chemotherapeutic agent. Compounds capable of inhibiting an efflux capability of a multidrug transporter also are disclosed.

4 Claims, 20 Drawing Sheets

SMALL MOLECULE INHIBITORS OF MRP1 AND OTHER MULTIDRUG TRANSPORTERS

CROSS-REFERENCE TO RELATED APPLICATION

This application claims the benefit of International Application No. PCT/US2005/016832, filed May 13, 2005, which claims the benefit of U.S. Provisional Patent Application No. 60/571,149, filed May 14, 2004.

BACKGROUND OF THE INVENTION

Drug resistance remains one of the primary causes of suboptimal treatment in cancer therapy. Multidrug resistance (MDR) is a type of resistance of cancer cells to multiple classes of chemotherapic drugs that can be structurally and mechanistically unrelated. Classic MDR involves an altered membrane transport that results in lower cell concentrations of a cytotoxic drug, and is related to an overexpression of a variety of proteins that act as ATP-dependent extrusion pumps.

Several members of different families of the ATP-binding cassette (ABC) superfamily of transport proteins are capable of transporting an extra ordinarily structurally diverse array of endo- and xenobiotics and their metabolites across cell membranes. Together, these transporters play an important role in the absorption, disposition, and elimination of these chemicals in the body. In tumor cells, increased expression of these drug transporters is associated with resistance to multiple chemotherapeutic agents.

P-glycoprotein (Pgp) and multidrug resistance protein-associated (MRP1) are the most important and most widely studied members of the ABC superfamily of transporters. MRPs that have been functionally characterized to date share the property of ATP-dependent export pumps for conjugates with glutathione (GSH), glucuronate, or sulfate.

MRP1 and MRP2 also mediate the cotransport of unconjugated amphiphilic compounds together with free GSH. MRP3 preferentially transports glucuronides, but not glutathione S-conjugates or free GSH. MRP1 and MRP2 also contribute to the control of the intracellular glutathione disulfide (GSSG) level. In addition to their role in cancer cell resistance, it is apparent that these proteins also have multiple physiological functions because they are expressed in many important nontumoral tissues and are largely present in prokaryotic organisms. It recently has been shown that MRP4 is able mediate resistance to irinotecan, which also is used to treat a range of cancers including neuroblastoma (Norris et al., *Mol. Cancer Ther.,* 4:547-53, 2005).

A number of drugs capable of reversing the effects of Pgp, MRP1, and sister proteins on multidrug resistance have been identified. The first MDR modulators discovered and studied in clinical trials possessed a definite pharmacological profile such that doses required to overcome MDR were associated with unacceptably high adverse side effects. As a consequence, considerable attention has been directed to developing more potent and selective modulators possessing the potency, selectivity, and pharmacokinetics such that the modulator can be administered at lower doses. Several novel MDR reversing agents (also known as chemosensitizers) are currently undergoing clinical evaluation for the treatment of resistant tumors. MDR and MDR modulators are discussed, for example, in A. Haimeur et al., *Curr Drug Metab.,* 5(1): 21-53 (2004); G. D. Leonard et al., Oncologist., 8(5):411-24 (2003); L. Homolya et al., *Biofactors,* 17(1-4):103-14 (2003); E. Teodori et al., *Farmaco,* 57(5):385-415 (2002); and J. Wijnholds, *Novartis Found Symp.,* 243:69-79 (2002).

Neuroblastoma (NB) is a disease that develops from the cells of the sympathetic nervous system, and is the most common solid tumor afflicting young children. The majority of patients possess a widely disseminated disease at diagnosis. Unfortunately, despite highly intensive treatment regimens, the prognosis for such patients is dismal with long-term survival rates of only 15% (2).

A number of prognostic markers have been identified for NB, including age at diagnosis, disease stage, histology, chromosome ip deletions, ploidy, and N-myc gene amplification (2). Of these, the number of copies of the N-myc oncogene in the tumor is one of the most powerful independent prognostic indicators of NB. N-myc gene amplification is demonstrated in 25% to 30% of primary untreated neuroblastomas, and numerous reports have confirmed that it is associated with a rapid tumor progresssion, an advanced clinical stage, and a poor treatment outcome (3). The risk of treatment failure in patients having tumors that display N-myc amplification is high, and the presence of this prognostic factor is often used as the basis for bone marrow transplantation (4).

However, despite dose-intensified combination chemotherapy regimens, including marrow ablative therapy, little real improvement in long-term survival of patients with N-myc gene amplification has been achieved (5). Therefore, devising a more effective therapy for high-risk NB patients remains a significant challenge, and alternate treatment strategies are urgently required.

Numerous laboratory studies have demonstrated that the N-myc oncogene critically contributes to the malignant phenotype of NB in vitro. Enhanced N-myc gene expression has been associated with increased growth potential and tumorigenicity (6), while the decreased N-myc gene expression that follows exposure of NB cells to retinoic acid is associated with growth inhibition and morphological differentiation (7).

Direct evidence for the critical role of the N-myc oncogene in this disease has come from a transgenic murine NB model developed by Weiss et al (8). These investigators placed the human N-myc oncogene under the control of the tyrosine hydroxylase promoter, resulting in the targeted expression of this oncogene specifically to neuroectodermal cells. The transgenic mice develop a murine equivalent of human NB, and the model mirrors human NB with respect to the site of the tumor and its metastases, the histology of the tumor, positive staining for NB-associated marker proteins, the formation in the tumor of synapses and the presence of neurosecretory granules, gains and losses of chromosomes in regions syntenic with those observed in human neuroblastoma, and a tumorigenesis that is affected by N-myc gene dosage. In addition, it recently was shown that the N-myc gene undergoes amplification in the majority of tumors from mice hemizygous for the transgene, highlighting the clinical relevance of this model (9). This model, therefore, is ideally suited to testing hypotheses regarding the specific mechanisms and pathways mediating the malignant phenotype of childhood NB, and also for investigating potential new therapeutic strategies.

While the mechanisms by which amplification of N-myc influences the prognosis of NB are not well defined, the N-myc oncogene encodes a 60-63 kDa nuclear phosphoprotein that contains a basic helix-loop helix/leucine zipper (bHLH-LZ) motif. N-myc acts as a transcriptional regulator and appears to play an important role in cellular proliferation, differentiation, transformation, and apoptosis (10, 11). For N-myc to activate transcription, it must first dimerize to MAX, another bHLH-LZ protein (12). Despite N-myc having been well characterized as a transcriptional regulator, the critical target genes responsible for the clinically aggressive phenotype of N-myc-amplified NB tumors remain largely unknown (13, 14).

Of the N-myc-regulated genes identified in the literature, however, one of the most important, particularly from a therapeutic perspective, is the MRP1 gene. This gene represents a potential therapeutic target because available evidence indicates that it is intimately associated with the malignant phenotype of this aggressive childhood cancer. Chemotherapeutic regimens used to treat NB generally involve a variety of compounds, including cisplatin, cyclophosphamide, and the naturally occurring lipophilic drugs, e.g., vincristine, doxorubicin, and VM-26. These latter drugs in particular have been shown to be substrates of MRP1.

The MRP1 gene encodes a 190-kDa membrane-bound glycoprotein that belongs to the superfamily of ATP-binding cassette (ABC) transmembrane transporters. The MRP family contains at least eight other members (15), and these proteins are particularly remarkable due to the range of compounds that they are able to transport, including natural product drugs, methotrexate, cisplatin, and nucleoside analogues (16).

Of all the MRP family members, MRP1 has been most closely linked to the development of clinical MDR for several types of cancer. Specifically, our research has provided strong evidence of a role for the MRP1 gene in mediating the drug resistant phenotype of NB. As a result, high expression levels of this gene are associated with a poor clinical outcome (17). Therefore, therapeutic suppression of these proteins, particularly MRP1, has a clinical potential in the treatment of cancer. To date, however, few effective and specific inhibitors of MRP1 are known. The present invention is directed to providing potent and highly specific MRP1 modulators that are capable of increasing sensitivity to a range of cytotoxic drugs in tumor cells overexpressing this gene.

It was shown that inhibition of MRP1 by AS-oligo sensitizes tumors to chemotherapy. In particular, MRP1 antisense (AS) oligonucleotides sensitized NB to chemotherapy in vivo in a mouse-human xenograft model of NB. The MRP1-antisense oligo reduced protein levels of MRP1 to an average of 40% of the nil treated controls (p=0.007). Significant chemosensitization to single-agent chemotherapy, VP16 (etoposide), at 1 µg/mL (p=0.035) and 10 µg/mL (p=0.02) compared to tumors not receiving oligonucleotides was observed. In contrast, MDR1-anti-sense oligo produced significant chemosensitization only at 10 µg/mL of VP16 (p=0.029). In addition; a downregulation of MRP1 also was associated with an increase in tumor cell death (79% increase in apoptosis index p=0.0313) and a reduction in cell-turnover (42% reduction in mitotic index p=0.0313), which was not observed with any other oligonucleotide. Thus, the detected sensitization to 1 µg/ml of VP-16 may result from the synergy of both effects, and MRP1 is theorized to play additional roles in the neuroblast function (PMID: 11857396).

Compared to control cells, MRP-AS transfectant cells demonstrated a higher proportion of dead and morphologically apoptotic cells, spontaneous neuritogenesis, and increased synaptophysin and neurofilament expression. Bcl-2 protein expression was markedly reduced in MRP-AS cells compared to controls. NB tumor cell line overexpressing the full-length MRP1 cDNA in sense orientation (MRP-S) demonstrated resistance to the neuritogenic effect of the differentiating agent, all-transretinoic acid. MRP1 expression in NB tumor cells may influence the capacity of NB cells for spontaneous regression in vivo through cell differentiation and death (PMID: 11720446).

In addition to NB, MRP1 (but not MDR1) was detected in gliomas and in normal astrocytes. In one study of two glioma cell lines, three other MRPs (MRP3, MRP4, and MRP5) were detected by RT-PCR in each cell line, whereas MRP2 was not expressed. In addition, the MRP3 protein also was detected by immunocytochemistry in both GL15 and 8 MG cell lines. Indomethacin (also a Cox-2 inhibitor) and probenecid, two modulators of MRP activity, increased the accumulation of vincristine and etoposide, each a substrate of MRPs, by both cell lines (PMID: 11857404).

Another study included cell lines and primary material. The drug-transporter proteins Pgp and MRP1 were expressed in cell lines (N=24) and primary cell cultures (N=36) from neuroectodermal tumors, as well as in brain tumor extracts (N=18) and normal human astrocytes (N=1). A significant expression of Pgp was relatively rare in glioma cells, in contrast to MRP1, which was constitutively overexpressed in cells derived from astrocytomas, as well as glioblastomas. Also, normal astrocytes cultured in vitro expressed high amounts of MRP1, but no detectable Pgp. Meningioma cells frequently coexpressed Pgp and MRP1, whereas most of the NB cell lines express higher Pgp levels, but lower MRP1 levels, compared to other tumor types.

Both a drug-exporting function and a chemoprotective function of Pgp and MRP1 can be demonstrated in selected tumor cells by a significant upregulation of cellular 3H-daunomycin accumulation and daunomycin cytotoxicity via administration of transporter antagonists. In summary, Pgp contributes to cellular resistance merely in a small subgroup of gliomas. In contrast, MRP1 plays a constitutive role in the intrinsic chemoresistance of gliomas and their normal cell counterparts (PMID: 12125964).

Intrinsic or acquired multidrug resistance is one of the major causes of treatment failure in human malignancy. Thus, it is not surprising that Pgp and MRP1 have been actively pursued as targets for therapeutic suppression. It is widely believed that safe and potent inhibitors of these proteins would be clinically efficacious in increasing the susceptibility of multidrug resistant cancers to chemotherapy.

Not surprisingly, because Pgp was discovered more than 15 years before MRP1, the vast majority of chemosensitizers characterized to date have been selected because of their ability to inhibit Pgp (reviewed in (18)). Unfortunately, the first and second generation of Pgp modulators yielded disappointing results when tested in the clinic.

First generation compounds, such as verapamil and cyclosporin, were chosen because they were known drugs and readily available. As expected from such compounds, their major drawback was an unacceptable level of toxicity. Thus, for verapamil, an associated cardiac toxicity made it impossible to achieve in vivo levels of drug that were found to be effective in vitro. Cyclosporin is associated with hepatic toxicity and nephrotoxicity.

As a result, in recent years, attention has been directed toward the development of more selective multidrug resistance modulators with high potency and low toxicity. There are several compounds that appear to be particularly promising, including LY 335979 and PSC 833 (or valspodar), each of which have entered phase II and III clinical trials, respectively (19, 20). However, each of these compounds are selective for Pgp and do not modulate MRP1 activity (18, 21). Although a few modulators have been identified that will inhibit both Pgp and MRP1, including VX-710, generally these compounds require unacceptably high concentrations to achieve effective modulation of MRP1 (18).

A number of MRP1-specific reversing agents have been identified in vitro including, for example, the leukotriene C4 antagonist MK571; the benzothiopene LY329146; the dihydropyridine analogue. NIK250; the quinilone antibiotic difloxacin, and the organic acids, sulfinpyrazone, benzbromarone, and probenecid (22). Some of these agents are illustrated below.

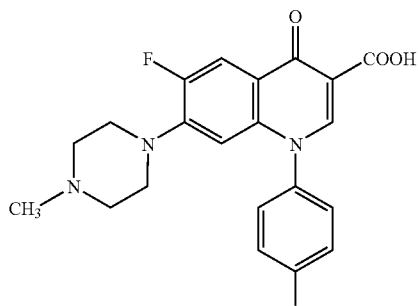

Difloxacin (quinolone) antimicrobial antibiotic

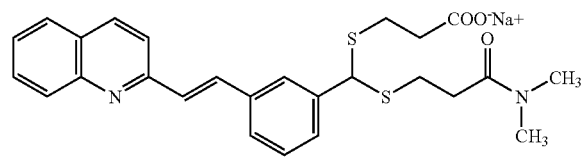

MK571 leukotriene C4 antagonist

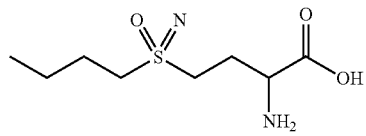

Buthionine sulfoximine (BSO)

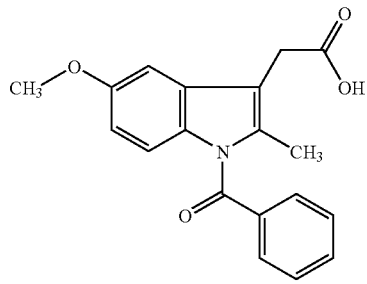

N-benzoyl analog of indomethacin

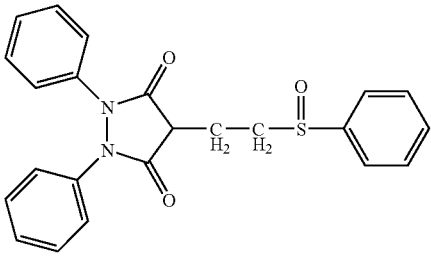

Sulfinpyrazone

-continued

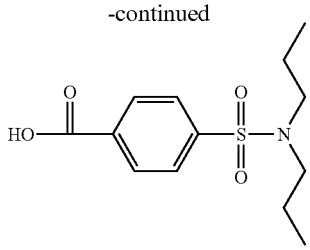

Probenecid

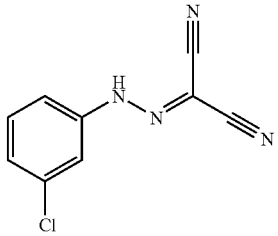

Carbonyl cyanide M-chlorophenyl hydrazone (CCCP)

In contrast to Pgp modulators, the identification of MRP modulators is still in its infancy due in large part to the gene having been cloned only about 10 years ago. Very few MRP modulators have appeared sufficiently effective to progress to clinical trial. Therefore, the search for highly specific and potent MRP-modulating agents is an important and ongoing area of research (23).

SUMMARY OF THE INVENTION

Cancer is the most common cause of death from disease in children. Among childhood malignancies, NB has one of the worst survival rates, indicating that new therapeutic strategies are urgently required. Fortunately, recent advances in the molecular genetics of NB have enabled the identification of several prospective molecular targets that provide opportunities for the development of new therapeutic strategies. Furthermore, highly representative animal models of spontaneous NB have been created, thus facilitating validation of new therapeutic approaches.

The present invention is directed to identifying compounds and new pharmaceutical compositions acting either by direct and specific killing of NB cells or by sensitizing tumors to conventional treatments.

In this regard, the N-myc gene has been defined as a key player in NB, and amplification of this oncogene has been shown to be a powerful predictor of treatment failure in childhood NB. Studies indicate that the aggressive drug resistant behavior of N-myc-amplified NB can be, at least, in part, associated with N-myc-mediated activation of MRP1, one of the multidrug transporters contributing to the drug resistant phenotype of neuroblastomas. In particular, we have shown that high-level MRP1 expression in primary NB is a powerful independent predictor of poor treatment results.

MRP1, therefore, was chosen as a primary gene target for developing new prospective antineuroblastoma pharmaceutical compositions from small molecules isolated by functional screening of chemical libraries in cell-based readout systems.

A powerful and safe MRP1 inhibitor has numerous other therapeutic applications in addition to sensitizing neuroblastomas because MRP1 has been shown to be involved in drug resistance of other types of cancer. Therefore, although the present application is directed primarily to a discussion of neuroblastomas, treatment of other cancers also are contemplated.

Therefore, one aspect of the present invention is to provide a method of potentiating the activity of a therapeutic drug, such as a chemotherapeutic drug or an antibiotic, in a cell or tissue comprising contacting the cell or tissue with a compound that inhibits an efflux capability of a multidrug transporter. The multidrug transporter can be a Pgp, LRP, or a member of the MRP family of transporters, for example, MRP1, MRP2, or MRP3. Preferably, the efflux capability of the multidrug transporter is selectively inhibited to retain the therapeutic drug in the cell or tissue, while maintaining normal efflux capability with respect to other compounds.

Another aspect of the present invention is to identify small molecules capable of inhibiting multidrug resistance of NB cells associated with MRP1. Another aspect of the invention is to utilize these compounds, or a composition containing one or more of these compounds, in the treatment of a cancer by the administration of a therapeutically effective amount of one or more of these compounds to an individual in need thereof.

Another aspect of the present invention is to provide a method of treating a cancer comprising administering to an individual in need thereof a therapeutically effective amount of a chemotherapeutic agent and an effective amount of a compound that modulates the activity of a multidrug transporter. The cancer can be a neuroblastoma, a renal cell carcinoma, or a colon cancer, for example.

Still another aspect of the present invention is to provide a method of sensitizing tumor cells to a chemotherapeutic agent in an individual undergoing a chemotherapeutic treatment regimen comprising administration of an effective amount of a compound that modulates the activity of a multidrug transporter. In preferred embodiments, the tumor cells overexpress MRP1 and/or the multidrug transporter is MRP1.

Yet another aspect of the present invention is to provide a method of determining an activity of a multidrug transporter comprising monitoring the function of a p53-reporter in a presence of a substrate for the multidrug transporter.

By screening a chemical library in a cell-based readout system, a new class of modulators of the multidrug transporter Pgp was identified, which, unlike previously known modulators, are not transporter substrates by themselves (1). Based on the methodology established herein, a new readout for the identification of compounds for modulating the activity of MRP1 was created and was used for screening a library of chemical compounds. This screening resulted in identification of compounds that act as powerful MRP1 inhibitors.

These and other novel aspects of the present invention will become apparent from the following, nonlimiting detailed description of the preferred embodiments.

DETAILED DESCRIPTION OF THE PREFERRED EMBODIMENTS

Because of their role in multidrug resistance of cancer, Pgp and other ABC transporters have been viewed mainly as targets for suppression. Accordingly, a number of Pgp inhibitors have been identified and tested (25). However, there is another potential practical application for Pgp that involves the use of its natural detoxifying function.

Figure 1:
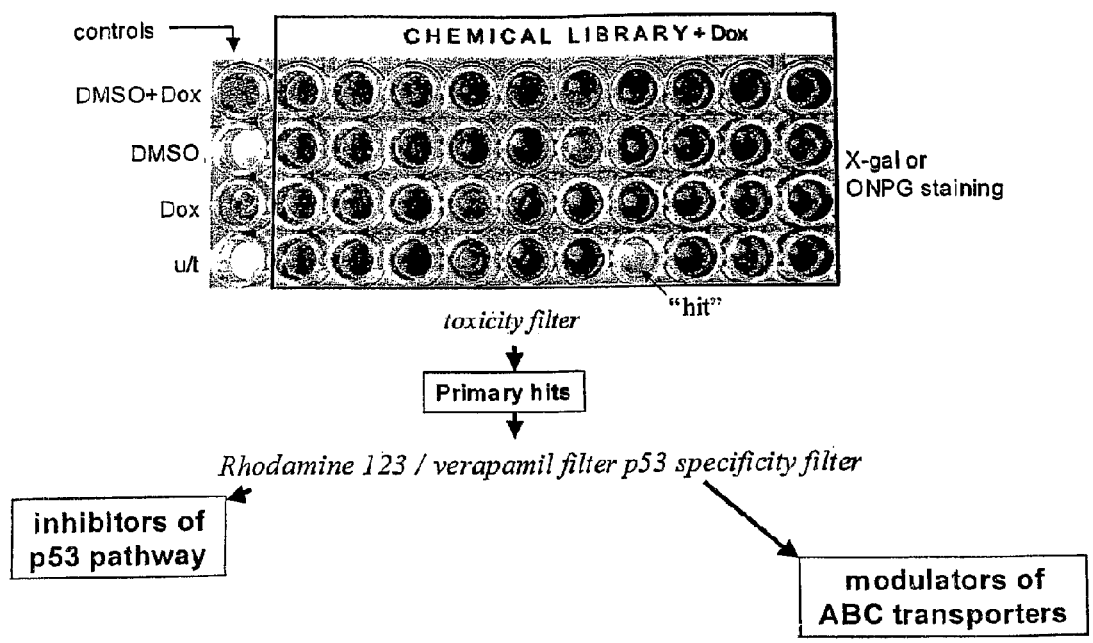
FIGS. 1-3 illustrate the screening process for identifying MDR transporter inhibitors.

Previous work indicated that among compounds identified for their ability to suppress p53 reporter activation in readout cells by doxorubicin (Dox), modulators of multidrug transporters capable of enhancing their drug efflux power existed (see FIG. 1). This observation led to a new readout system allowing a systematic search for specific MDR transporter inhibitors.

By screening a chemical library for compounds that protect cells from the Pgp substrate adriamycin (Adr), a series of small compounds that interfered with the accumulation of Adr in mouse fibroblasts by enhancing efflux of Adr was identified. The identified compounds also stimulated efflux of Rhodamine 123 (Rho123), another substrate of multidrug transporters. Stimulation of drug efflux was detectable in the cells expressing Pgp, but not in their Pgp-negative variants, and was completely reversible by the Pgp inhibitors.

A dramatic stimulation of Pgp activity against Adr and Rho123 by the identified compounds was accompanied by suppression of Pgp-mediated efflux of other substrates, such as taxol or Hoechst 33342, indicating that the compounds are modulators of substrate specificity of Pgp. Consistently, Pgp modulators dramatically altered the pattern of cross resistance of Pgp-expressing cells to different Pgp substrates, i.e., an increase in resistance to Adr, daunorubicin, and etoposide was accompanied with cell sensitization to Vinca alkaloids, gramicidin D, and taxol, with no effect on cell sensitivity to colchicine, actinomycin D, puromycin, and colcemid, as well as to several non-Pgp substrates. The relative effect of Pgp modulators against different substrates varied among the identified compounds that can be used as excellent tools for analyzing mechanisms of drug selectivity of Pgp. Importantly, the identified compounds belong to a new functional class, unlike "classic" inhibitors, such as verapamil, reserpine, and cyclosporine A, because they are not by themselves substrates for the transporters.

These results allow addressing the problem of rational control over cell sensitivity to drugs and toxins by small molecules acting through a new mechanism of modulation of ABC transporters. As a result, the effect of the identified compounds on drug sensitivity of cells of renal cell carcinoma (RCC), representing one of the most drug resistant types of cancer, was tested. It was found that several compounds were as active as verapamil in sensitizing RCC cells to taxol, but clearly acted through a different mechanism, causing no effect on sensitivity to doxorubicin. See FIG. 2, which illustrates the principle of the read out system.

We hypothesized that a library of compounds sharing structural similarity with a new class of modulators of Pgp might be enriched with modulators of ABC transporters which could play important role in drug sensitivity of tumors. To test this hypothesis, the effect of various compounds belonging to this new class on other ABC transporters was tested, and it was found that they are active against other members of the transporter family, as discussed herein for MRP1. This allowed us to view this focused library as a valuable source of new compounds for modulating activity of a broad range of transmembrane pumps.

Another feature of the present invention is the discovery of a new approach for identifying ABC transporter modulators by screening chemicals in cell-based readout system that can sense drug presence inside the cell by activating p53-responsive construct. This approach was used to identify the present MRP1 inhibitors.

Figure 2:
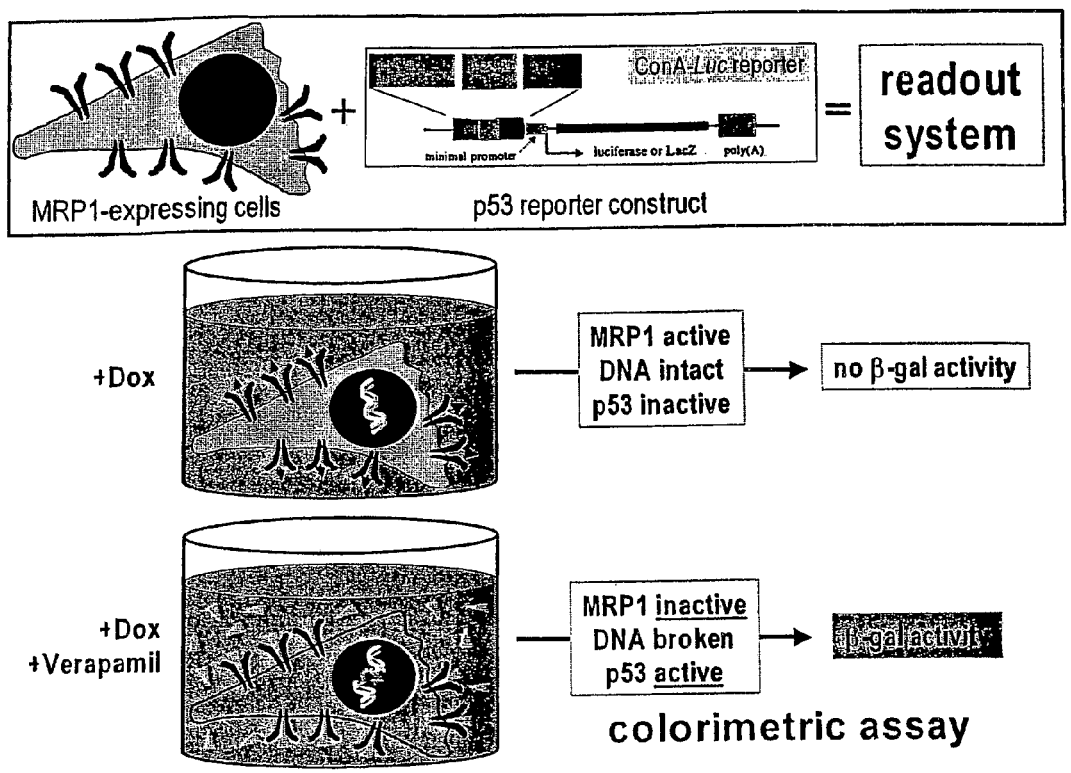
Figure 3:
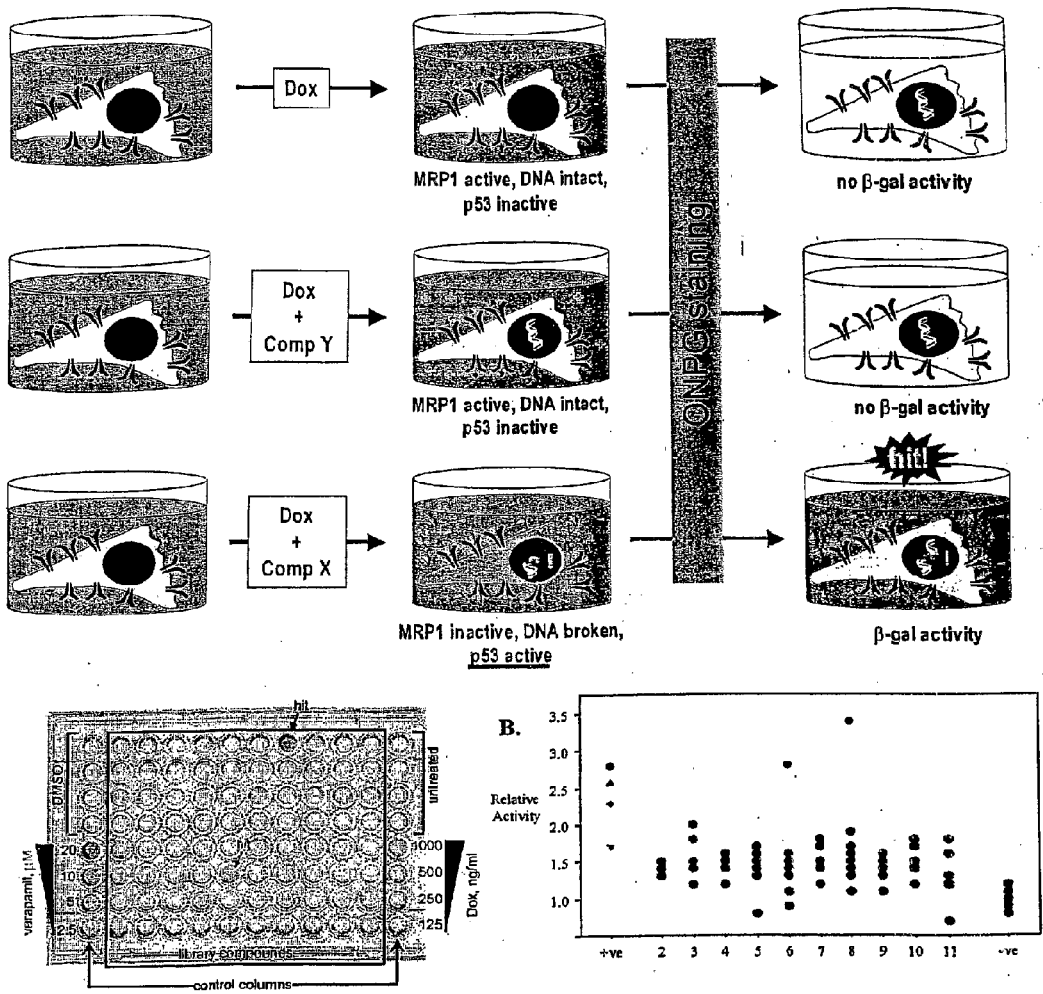

In a search for small molecule inhibitors of MRP1, a library of over 2,300 compounds, specifically designed around ABC transport modulators was screened. A critical aspect of screening for small molecule inhibitors of a given gene target involves development of a "read out" system or assay for growth inhibition that must be determined on a gene-by-gene basis, and which depends on the nature of the candidate gene. FIGS. 1-3 illustrate the "read out" system utilized in the present invention.

As a read out system for inhibitors of MRP1, the highly drug resistant MCF7/VP breast cancer cells (24), which have amplified and overexpressed MRP1, but negligible Pgp expression, were transfected with a p53 responsive reporter containing the LacZ gene. The drug-sensitive parental MCF7 cells also were transfected with this construct. Treatment of these latter cells with doxo rubicin (Dox) led to the activation of the p53 way due to induction of DNA damage by the cytotoxic agent, and in turn, marked induction of LacZ. However, treatment of the MCF7/VP LacZ transfectant population resulted in negligible induction of LacZ because the high levels of MRP1 present in these cells resulted in greatly reduced intracellular accumulation of doxorubicin, which in turn means that p53 was not activated. We, therefore, were interested in small molecule compounds that inhibit MRP1 in MCF7/VP LacZ cells, with such inhibitors being identified by a doxorubicin-induced activation of the reporter.

Functional screening was performed in 96-well plates containing MCF-7/VP/LacZ cells. A combination of doxorubicin and compounds from the library were added 24 hours after plating. After an additional 24 hours, the 3-galactosidase substrate o-nitrophenyl-beta-D-galactopyranoside (ONPG) was added prior to measuring color development at 405 nm. In this system, compounds that significantly inhibited or interfered with MRP-mediated efflux of doxorubicin provide a p53-dependent expression of LacZ, which is detectable as an enhanced yellow color by comparison with other wells. A number of controls were used, including wells with doxorubicin alone (negative controls), and, as positive controls, wells containing increasing concentrations of verapamil, a broad spectrum ABC transporter inhibitor.

Following screening of the 2300 compound library, inhibitor compounds were identified by spectrophotometric quantitation of the intensity of color in each well. An example of the results obtained from one of these plates, containing two hits, is shown in FIG. 3. Each of these compounds yielded higher induction of LacZ than that observed with the highest concentration of verapamil (i.e., 20 μM). The compounds also were tested in a p53 inhibitory assay using MCF7 wild-type cells and shown to be functioning by affecting MRP1 and not by directly activating a p53 response (see FIG. 4).

The identified inhibitor compounds have the following structures:

| Compound No. | |
|---|---|
| 3H05 | 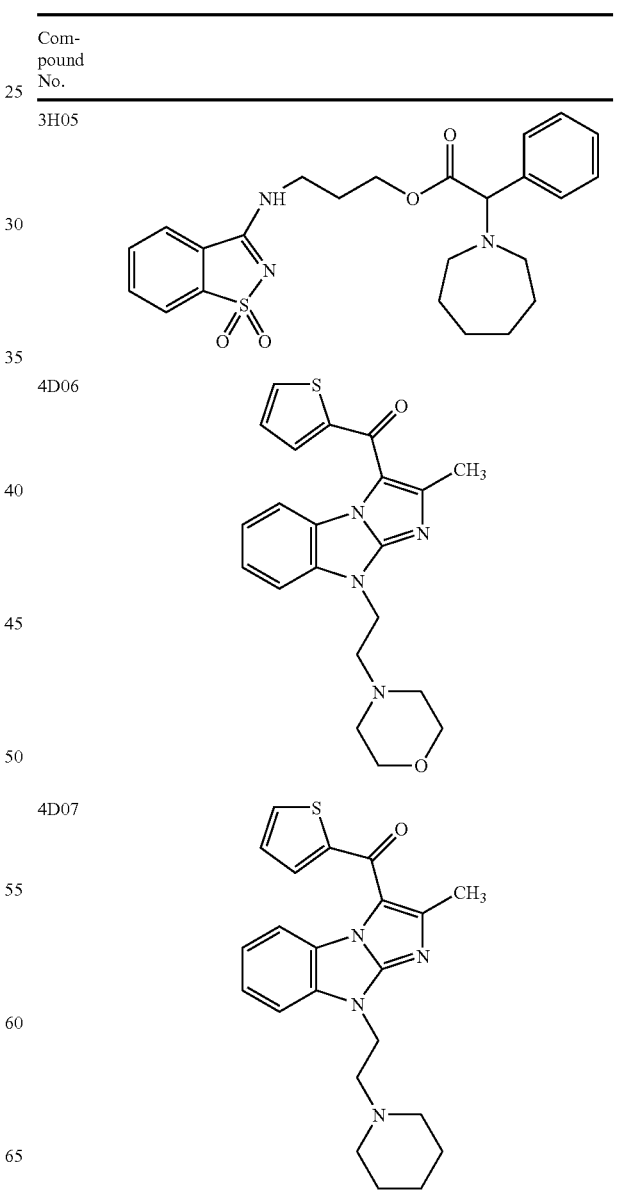 |
| 4D06 | |
| 4D07 | |

| Compound No. | | Compound No. | |
|---|---|---|---|
| 4E07 | 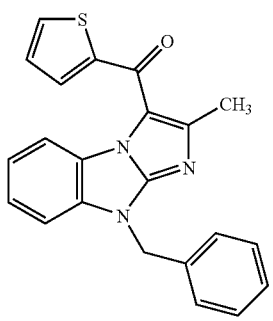 | 9C06 | 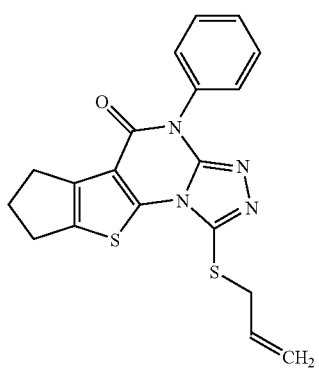 |
| 4E10 | 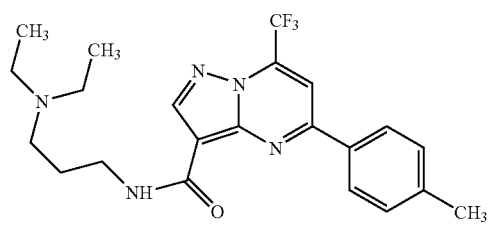 | 14C08 | 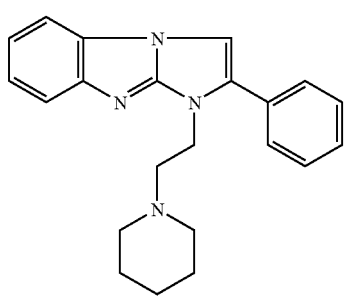 |
| 4E11 | 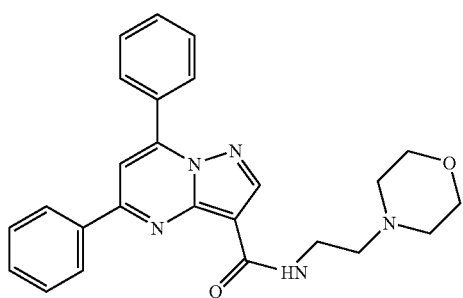 | 19B04 | 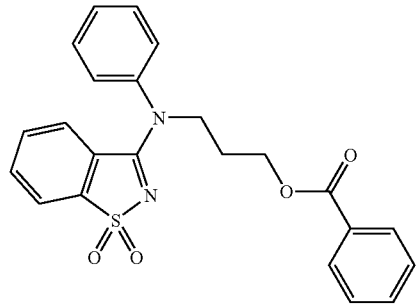 |
| 4G05 | 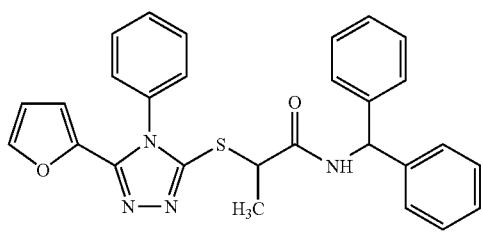 | 25E10 | 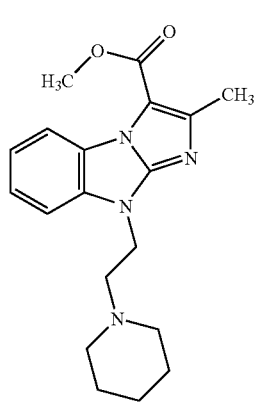 |
| 4H10 | 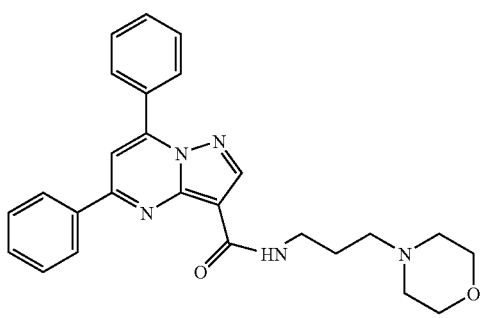 | | |

-continued

| Compound No. | |
|---|---|
| 17A08 | 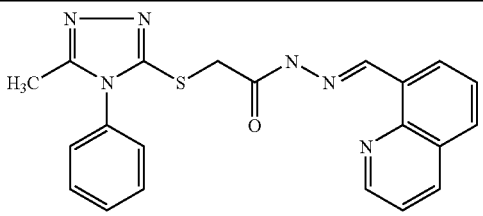 |
| 27G06 | 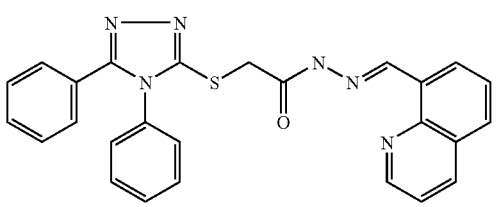 |
| 13A02 | 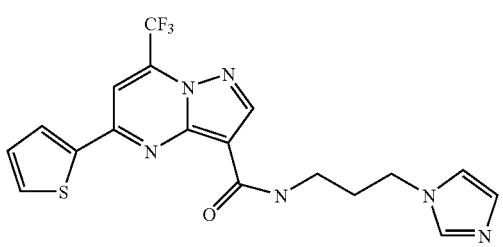 |
| 12E03 | 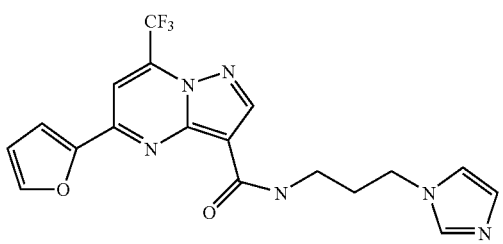 |

Also useful in the methods of the present invention are prodrugs; salts, and hydrates of the above compounds, and mixtures of these compounds.

More particularly, FIG. 3 illustrates the identification of potential small molecule inhibitors of MRP1. MCF7/VP cells containing the LacZ reporter were treated with doxorubicin (0.5 μg/ml) in the presence of library compounds. LacZ induction, indicating reduced MRP activity, was detected by increased ONPG staining. FIG. 3(A) is a scan of one of the 96-well plates showing two "hits" (arrowed). In FIG. 3(B)., a quantitative read out of ONPG staining is provided, with each column (2-11) showing the results obtained for 8 individual test compounds (8×10=80 compounds), corresponding to columns 2-11 on the microtitre plate shown in Panel A. The positive control column displays the results obtained with an increasing concentration of verapamil 2.5 μM; 5 μM; 10 μM; and 20 μM), while the negative controls are wells containing varying concentrations of doxorubicin alone. The two hits had values that were above the value of the 20 μM verapamil control.

Figure 4:
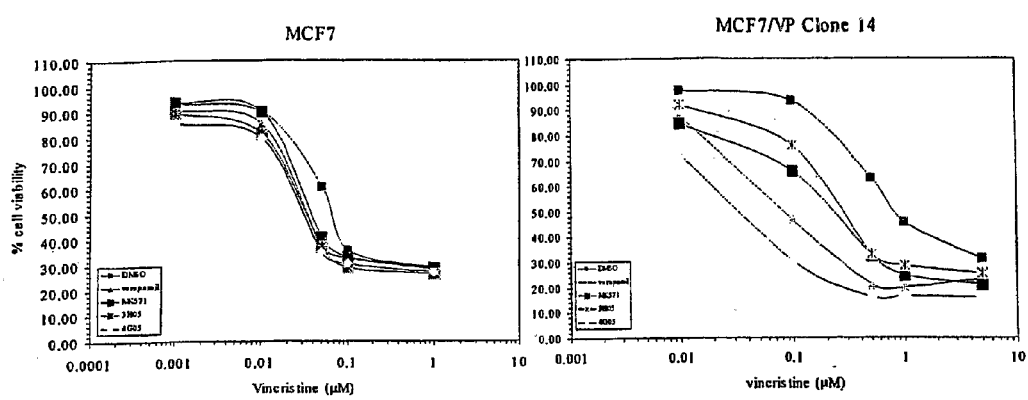
FIG. 4 contains plots of % cell viability vs. vincristine concentration (μM) showing sensitization of MRP1 expressing cells (MCF7/VP) but not the original MCF7 cell line to vincristine by MDR transporter inhibitors.

FIG. 4 shows that identified compounds can sensitize MRP1-expressing cells (MCF7/VP, clone 14), but not original cell line (MCF7), to vincristine. Cells in 96-well plates ($5 \times 10^3$ per well) were incubated with different concentrations of vincristine in the presence of 5 μM of the candidate compounds for 3 days. Cell numbers then were estimated using methylene blue assay. Curves show vincristine dose dependence of cell number per well in relation to the number of cells growing in drug-free conditions. Verapamil (10 μM) was used as control. Similar results were obtained with doxorubicin.

TABLE 1

Summary of the effects of identified compounds on sensitivity of MRP1-expressing cells to different chemotherapeutic drugs
Substrate specificity of several identified compounds (folds of sensitization of MCF7/VP cells to different drug)

| | Drug | | | |
|---|---|---|---|---|
| Compound | doxorubicin | vincristine | etoposide | cisplatin |
| verapamil | 2.5 | 9.0 | 8 | 1.05 |
| 4H10 | 3.8 | 14.2 | 58 | 1.2 |
| 4E10 | 3.2 | 12 | 27 | 1.25 |
| 4E11 | 2.7 | 10.5 | 34 | 1.1 |
| 19B04 | 3.5 | 12.5 | 10 | 1.3 |
| 9C06 | 3.3 | 16 | 12 | 1.5 |
| 4G05 | 1.6 | 3 | 2 | 1.1 |
| 14C08 | 4.0 | 14 | 18 | 1.05 |
| 17A08 | 3.6 | 3 | 5 | 1.1 |

TABLE 2

Summary of the effects of identified compounds on sensitivity to doxorubicin of cells expressing different types of multidrug transporters
Transporter specificity of several identified compounds (folds of sensitization of doxorubicin)

| | Drug | | | |
|---|---|---|---|---|
| Compound | MRP1 | MRP2 | MDR1 | MDR3 |
| verapamil | 1.6 | 1.3 | 3.3 | 0.8 |
| 4H10 | 4.1 | 3.3 | 4.5 | 0.9 |
| 4E10 | 3.7 | 7 | 2.0 | 0.6 |
| 4E11 | 3.9 | 6.5 | 4.2 | 0.7 |
| 19B04 | 2.5 | 2.2 | 1.2 | 0.5 |
| 9C06 | 3.3 | 4.3 | 3.7 | 0.4 |
| 4G05 | 1.75 | 1.5 | 4.6 | 2.4 |
| 14C08 | 3.0 | 1.3 | 3.7 | 0.6 |
| 17A08 | 1.1 | 1.4 | 2 | 1.3 |

Figure 5:
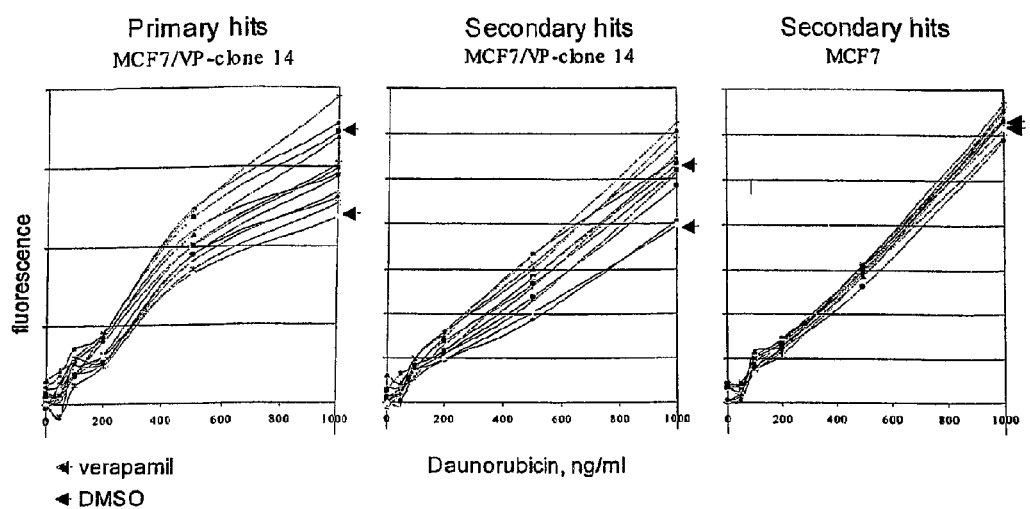
FIG. 5 contains plots of fluorescence vs. daunorubicin concentration (ng/ml) showing a classification of hits in the screening procedure.

FIG. 5 contains a classification of the identified compounds using a drug accumulation assay. Cells expressing MRP1 were incubated with the indicated concentrations of daunorubicin for 2 hours and cell fluorescence was measured by FACS. As control, original MCF7 cells low expression of MRP1) were used. Verapamil was used for comparison. The majority of hits (primary) were weaker than verapamil, while many of hits (second ary) are more potent than verapamil.

Figure 6:
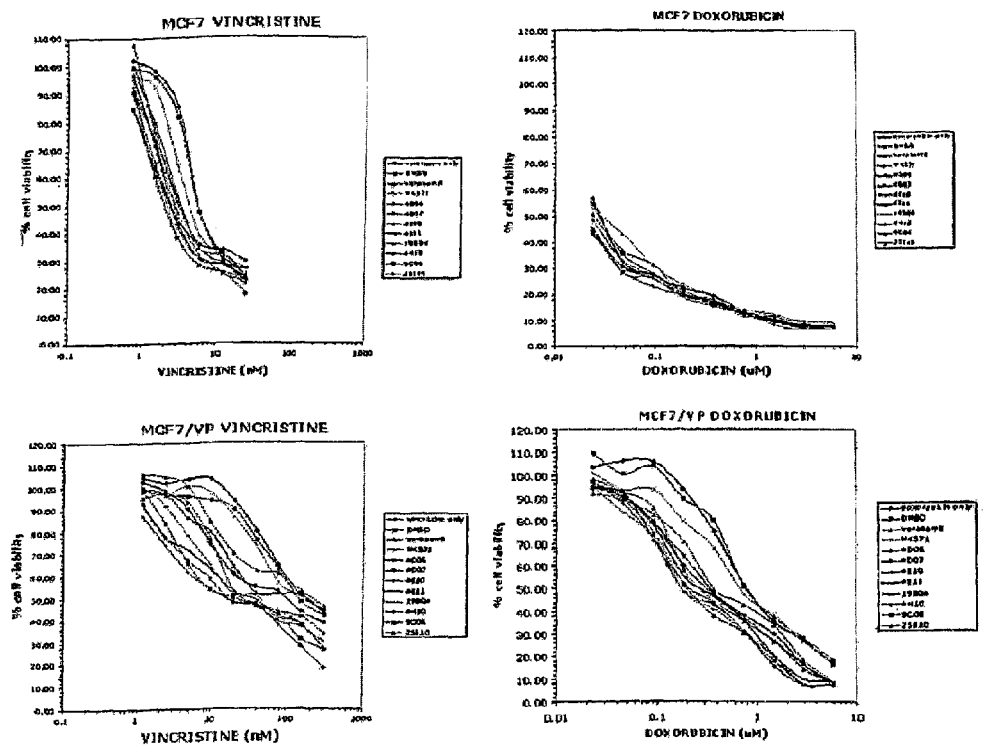
FIG. 6 contains plots of % cell viability vs. concentration of vincristine (nM) or doxorubicin (μM) showing the effect of MDR transporter inhibitors on cell sensitivity.

FIG. 6 illustrates the effect of the identified inhibitor compounds on cell sensitivity to doxorubicin and vincristine. Cells (with or without MRP1 expression) were incubated 24 hours with the indicated concentrations of vincristine or doxorubicin followed by incubation for additional 48 hours in drugfree media. Cell numbers were quantified by standard methylene blue assay. Only a minor sensitizing effect was observed in the original MCF7 cells. Many of the present compounds were found to be more potent inhibitors than verapamil.

Figure 7:
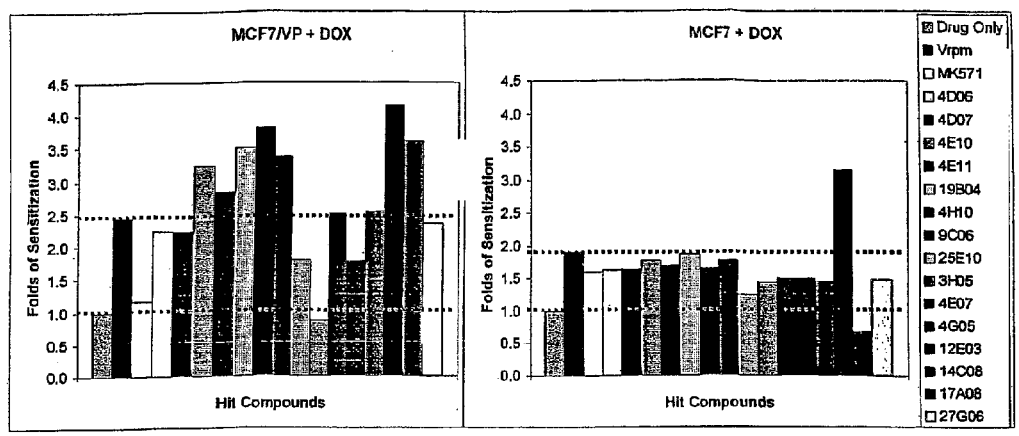
FIGS. 7-10 contain plots of fold sensitivity to MDR transporter inhibitors showing the effect of the inhibitors on the sensitivity of MRP1-positive and MRP1-negative cells to doxorubicin, vincristin, etoposide, taxol, and cisplatin, respectively.

FIG. 7 illustrates the effects of the identified inhibitor compounds on the sensitivity of MRP1-positive and MRP1-negative cells to doxorubicin. Fold of sensitization is calculated as a ratio of $LD_{50}$ in the presence and in the absence of the inhibitor compound (see FIG. 6). Cell sensitivity with no transporter modulators and in the presence of verapamil are shown by dotted lines.

Figure 8:
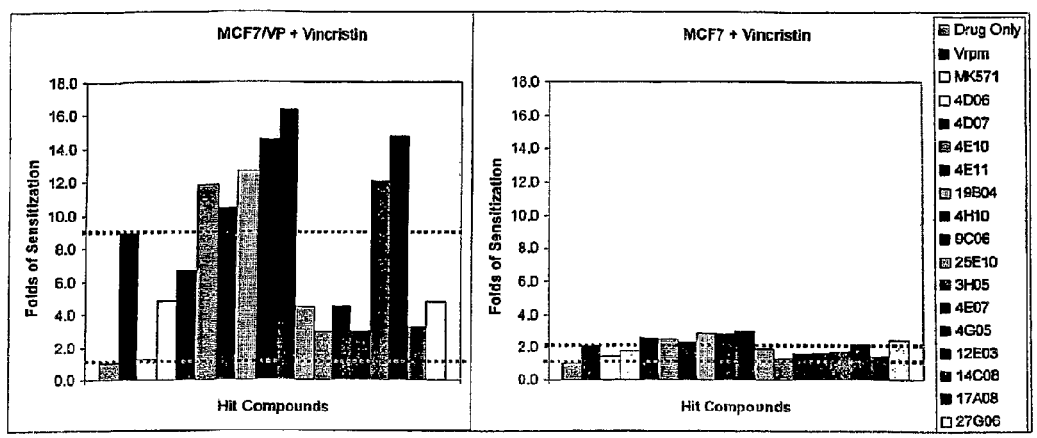

FIG. 8 illustrates the effects of the identified inhibitor compounds on sensitivity of MRP1-positive and MRP1-negative cells to vincristine. Fold of sensitization again is calculated as the ratio of $LD_{50}$ in the presence and in the absence of the inhibitor compound (see FIG. 6). Cell sensitivity with no transporter modulators and in the presence of verapamil are shown by dotted lines.

Figure 9:
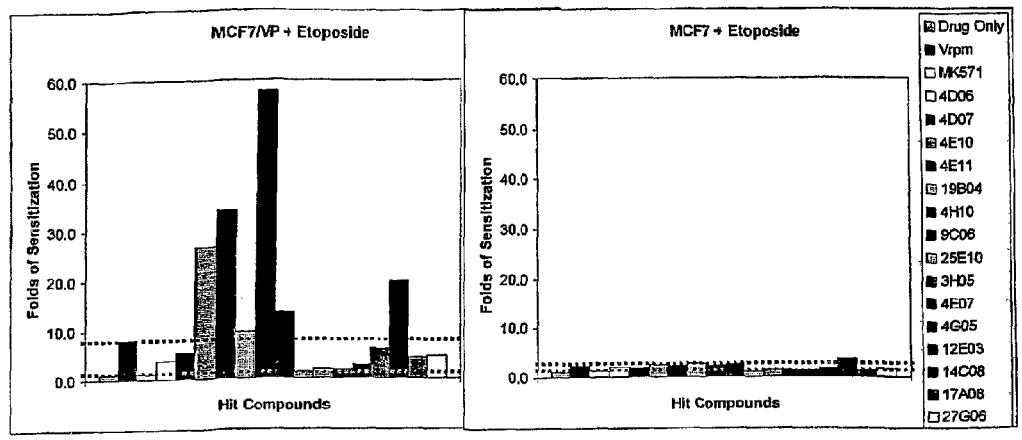

FIG. 9 illustrates the effects of the identified inhibitor compounds on sensitivity of MRP1-positive and MRP1-negative cells to etoposide. Fold of sensitization again is calculated as the ratio of $LD_{50}$ in the presence and in the absence of the inhibitor compound (see FIG. 6). Cell sensitivity with no transporter modulators and in the presence of verapamil are shown by dotted lines.

Figure 10:
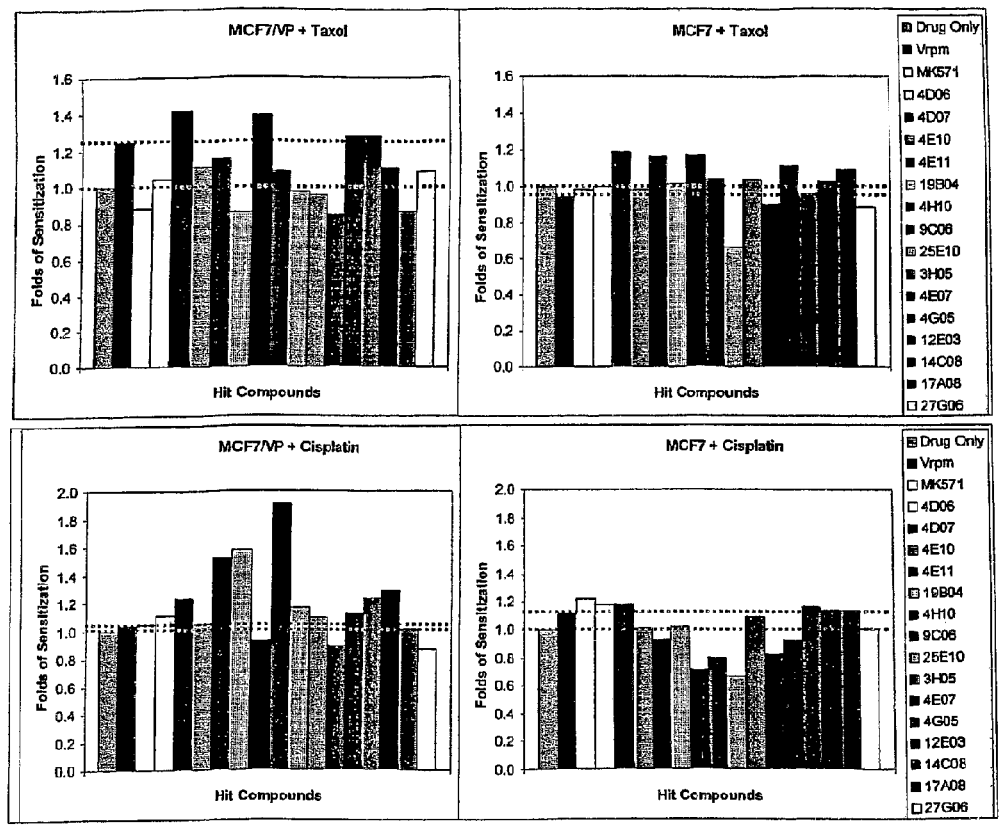

FIG. 10 illustrates the effects of the identified inhibitor compounds on sensitivity of MRP1-positive and MRP1-negative cells to taxol and cisplatin. Fold of sensitization again is calculated as the ratio of $LD_{50}$ in the presence and in the absence of the inhibitor compound (see FIG. 6). Cell sensitivity with no transporter modulators and in the presence of verapamil are shown by dotted lines. Lack of sensitizing effect is expected because neither taxol nor cisplatin are substrates of MRP1.

Figure 11:
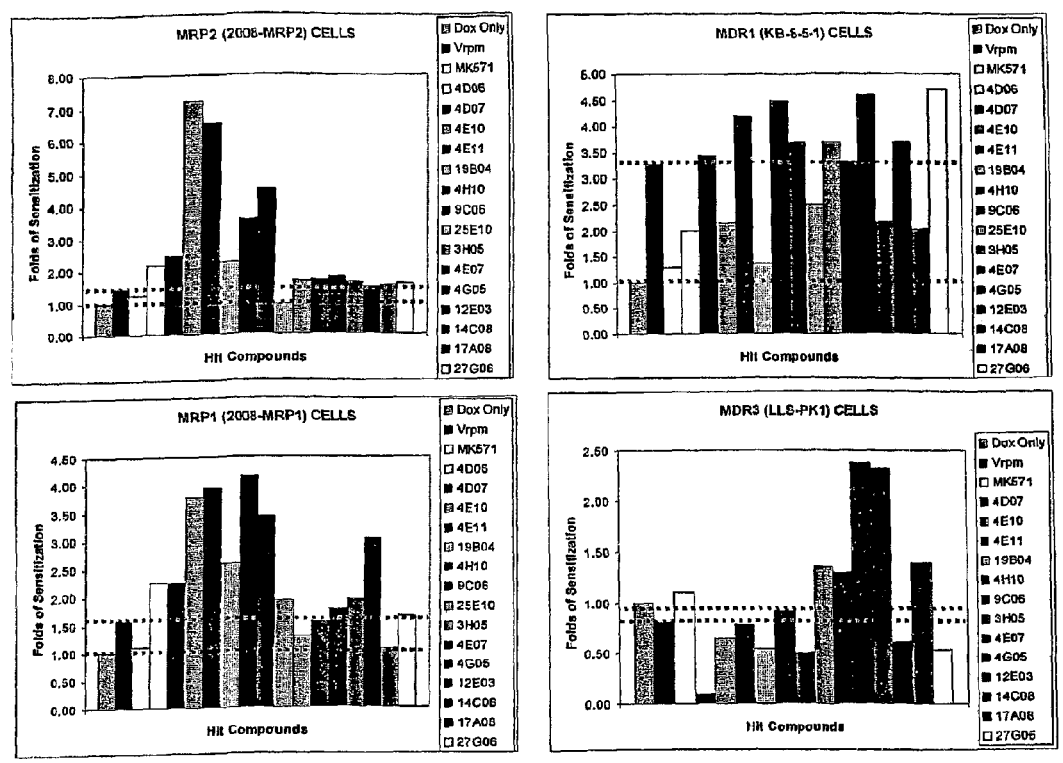
FIG. 11 contains plots of fold sensitivity to MDR transporter inhibitors showing the effect of the inhibitors on the sensitivity of cells expressing the indicated multidrug transporter to doxorubicin.

FIG. 11 illustrates the effects of the identified inhibitor compounds on the sensitivity of cells expressing the indicated multidrug trans-porters to doxorubicin, which is known to be a substrate for each of these transporters. Fold of sensitization again is calculated as the ratio of $LD_{50}$ in the presence and in the absence of the inhibitor compound (see FIG. 6). Cell sensitivity with no transporter modulators and in the presence of verapamil are shown by dotted lines. From the data in FIG. 11, it can be concluded that (a) the majority of the identified inhibitor compounds have an effect on more than one transporter; (b) many of the compounds are more potent than verapamil; and (c) some compounds exhibit a preferential effect against specific transporters.

Figure 12:
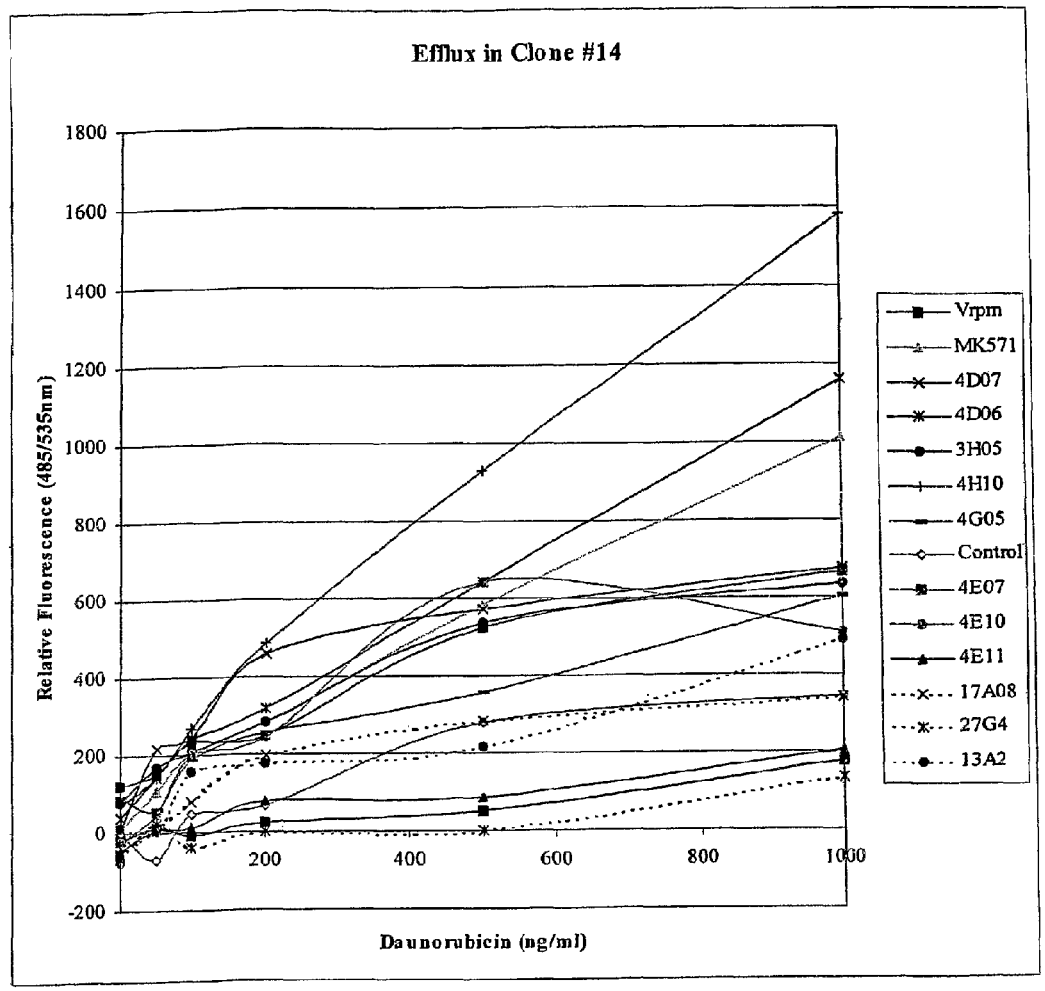
FIG. 12 contains plots of relative fluorescence to daunorubicin concentration (ng/ml) classifying. MDR inhibitors according to potency inhibition of doxorubicin efflux.

FIG. 12 classifies the identified inhibitor compounds according to their strength as inhibitors of doxorubicin efflux by MRP1. Cells were treated with daunorubicin in the presence of a test compound or a control for 2 hours, followed by incubation in fresh drug-free medium for 1 hour. Retained daunorubicin levels were measured to determine the effect of the inhibitor compounds on efflux activities. Compound 4H10 was found to be the most potent inhibitor.

Figure 13:
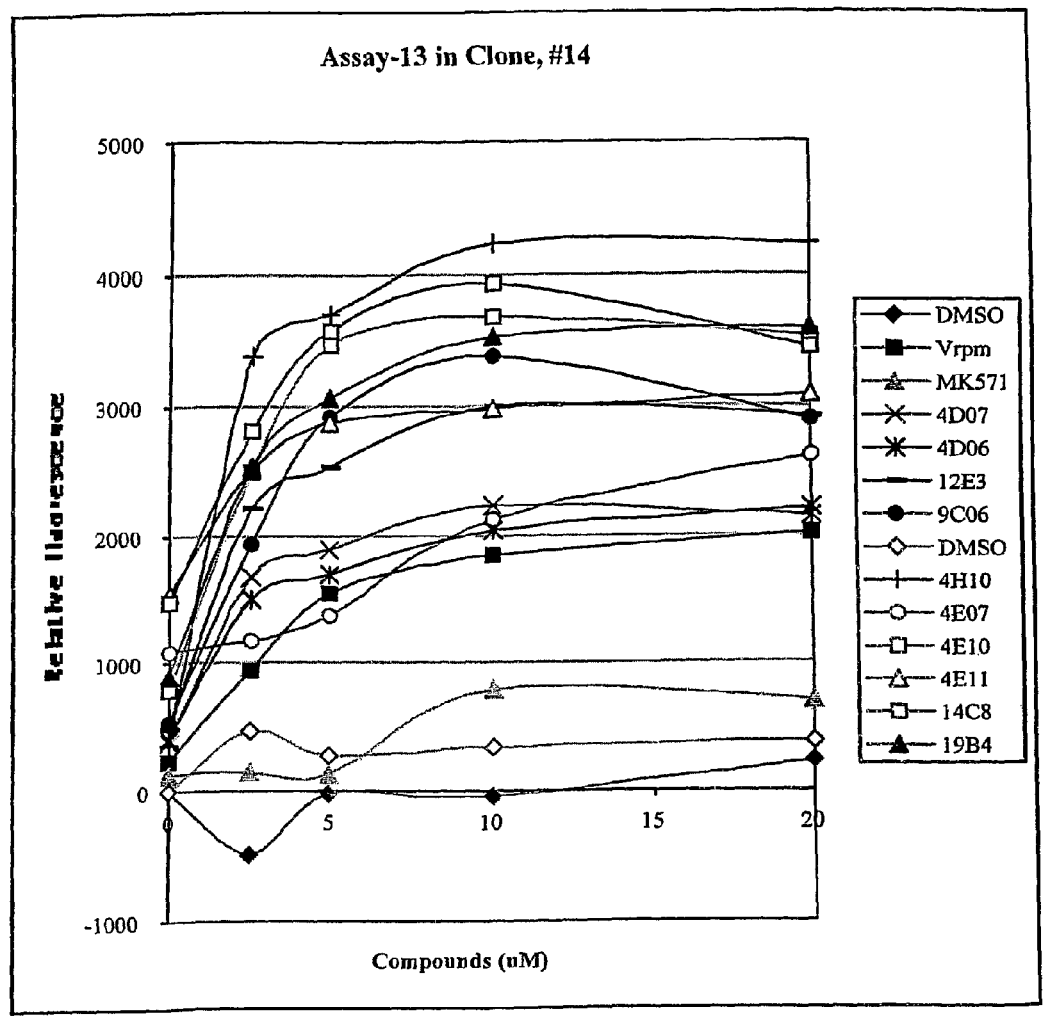
FIG. 13 contains plots of relative fluorescence vs. MRP1 inhibitor concentration (μM)

FIG. 13 classifies the identified inhibitor compounds according to their potency in dose-dependence experiments. No significant variations in this property were found. All identified inhibitor compounds reached a plateau in activity at about 1 to about 5 µM.

Figure 14:
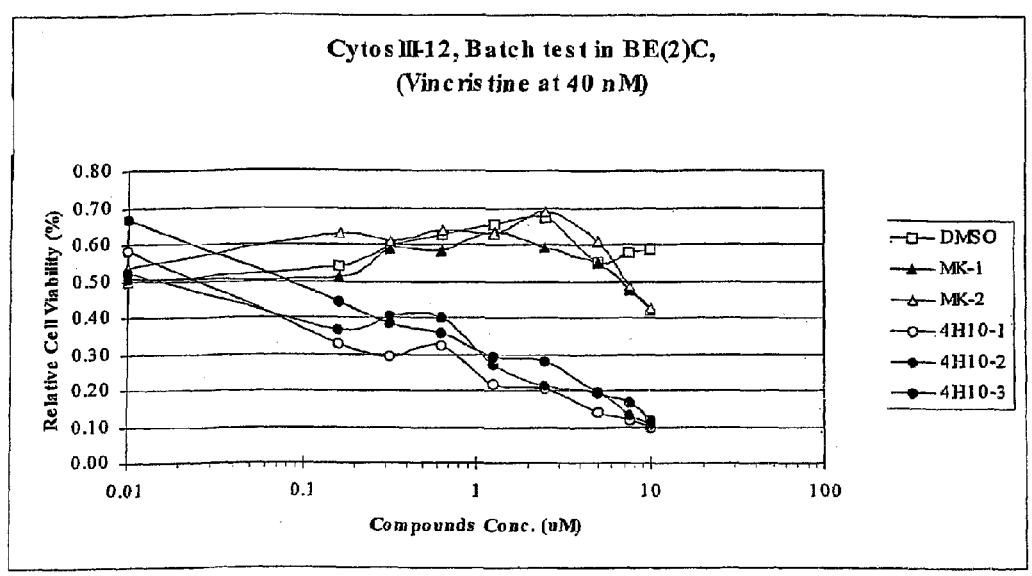
FIG. 14 contains plots of relative cell viability (%) vs. inhibitor concentration (μM) comparing a present inhibitor compound 4H10 to a prior MRP1 inhibitor MK571.

FIG. 14 summarizes a determination of dose dependence of drug, sensitization effect of compound 4H10 compared to the conventional MRP1 inhibitor MK571. Three different lots of 4H10 showed effects in submicromolar concentrations, and using this parameter are about 100 times more potent than MK571.

Figure 15:
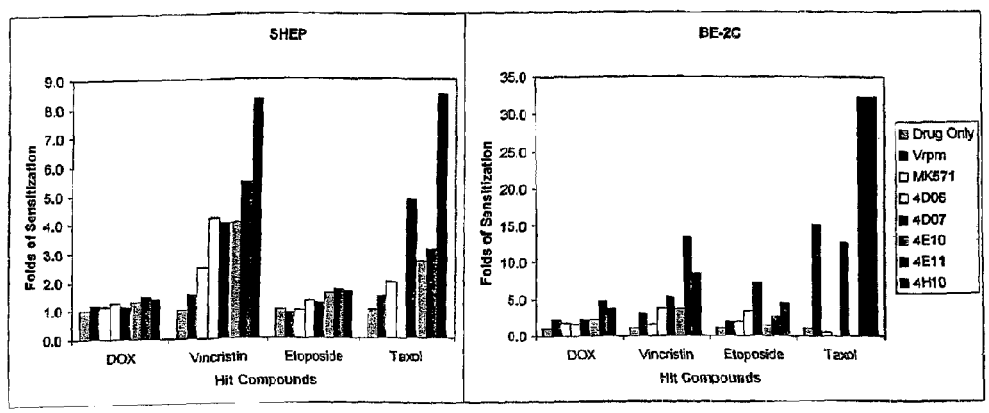
FIGS. 15-17 contains plots of fold sensitization for present MRP1 inhibitors on the sensitivity of NB cell lines, renal cell carcinoma, and colon carcinoma cell lines, respectively, to four chemotherapeutic drugs.

FIG. 15 shows the effect of the identified inhibitor compounds on sensitivity of neuroblastoma cell lines to four chemotherapeutic drugs. Fold of sensitization is calculated as the ratio of $LD_{50}$ in the presence and in the absence of the inhibitor compound (see FIG. 6). Strong sensitization to taxol, which is not an MRP1 substrate, indicates that these cells express transporters other than MRP1.

Figure 16:
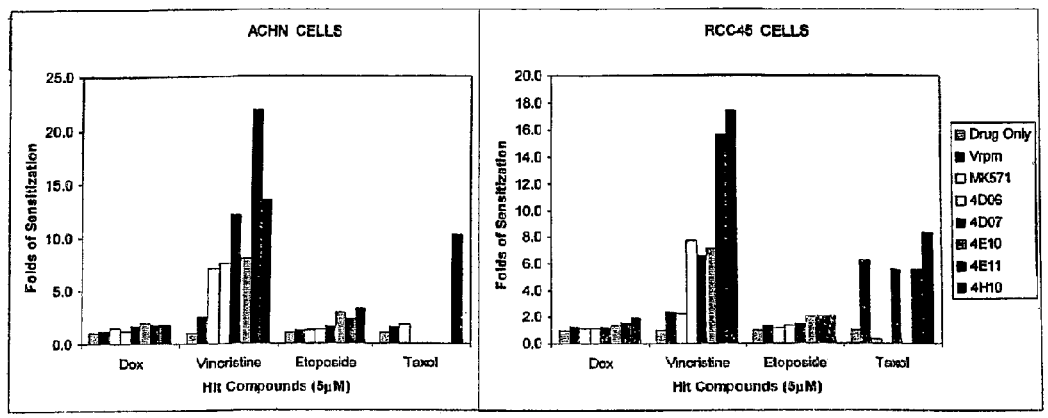

FIG. 16 shows the effect of the identified inhibitor compounds on sensitivity of renal cell carcinoma lines to four chemotherapeutic drugs. Fold of sensitization again is calculated as the ratio of $LD_{50}$ in the presence and in the absence of the inhibitor compound (see FIG. 6). Strong sensitization to taxol, which is not an MRP1 substrate, indicates that these cells express transporters other than MRP1.

Figure 17:
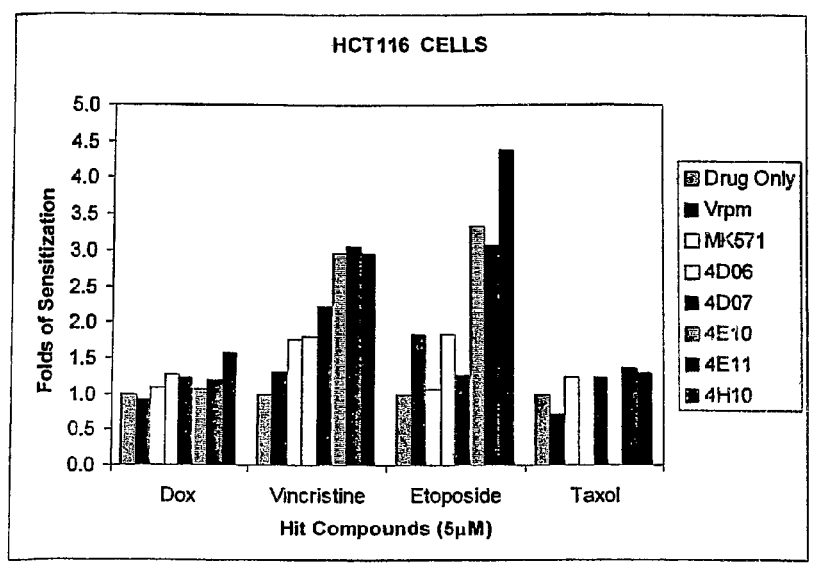

FIG. 17 shows the effect of the identified inhibitor compounds on sensitivity of colon carcinoma cell lines to four chemotherapeutic drugs. Fold of sensitization again is calculated as the ratio of $LD_{50}$ in the presence and in the absence of the compound (see FIG. 6). From FIGS. 15-17, it can be concluded that the identified inhibitor compounds strongly sensitize tumor cells of different origin to a variety of chemotherapeutic drugs.

Figure 18:
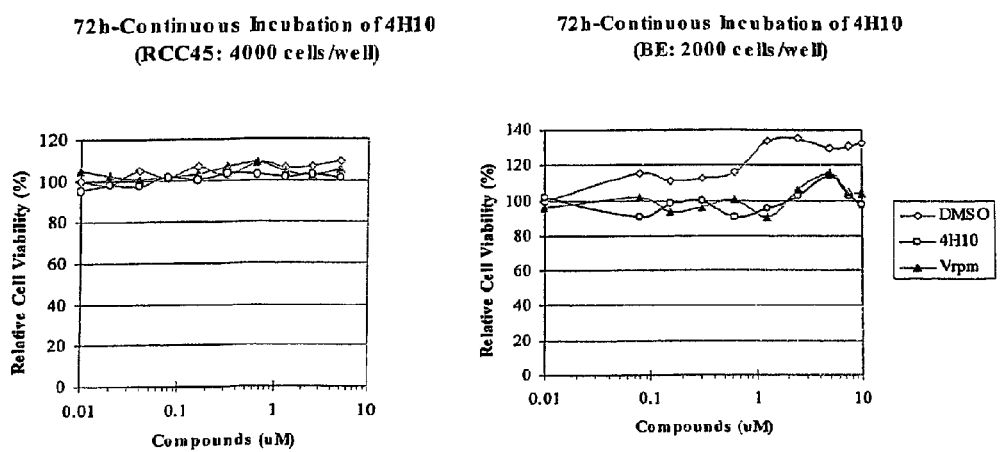
FIG. 18 contains plots of cell viability vs. concentration of compound 4H10 showing no direct toxicity of the compound toward NB cell lines.

FIG. 18 illustrates that no direct toxicity of different lots of compound 4H10 against NB cells is observed.

Figure 19:
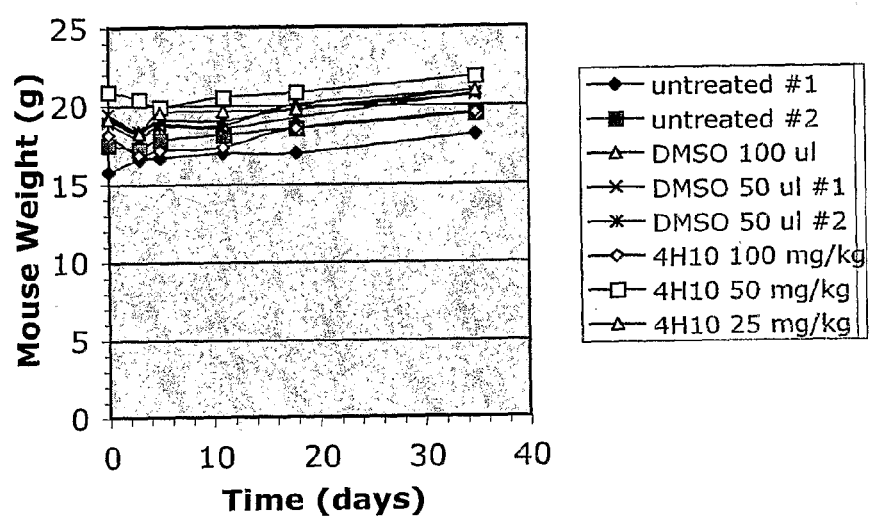
FIG. 19 contains plots of mouse weight (g) vs. days showing no in vivo toxicity of compound 4H10 after 30 days observation following injection.

FIG. 19 shows a lack of in vivo toxicity of compound 4H10 (up to 100 mg/kg) after 30 days of observation following a single i.p. injection. In particular, one parameter for testing toxicity is a weight loss of greater the 100 of the body weight of a test mouse. Compound 4H10 did not adversely affect mouse weight, as illustrated in FIG. 19.

Figure 20:
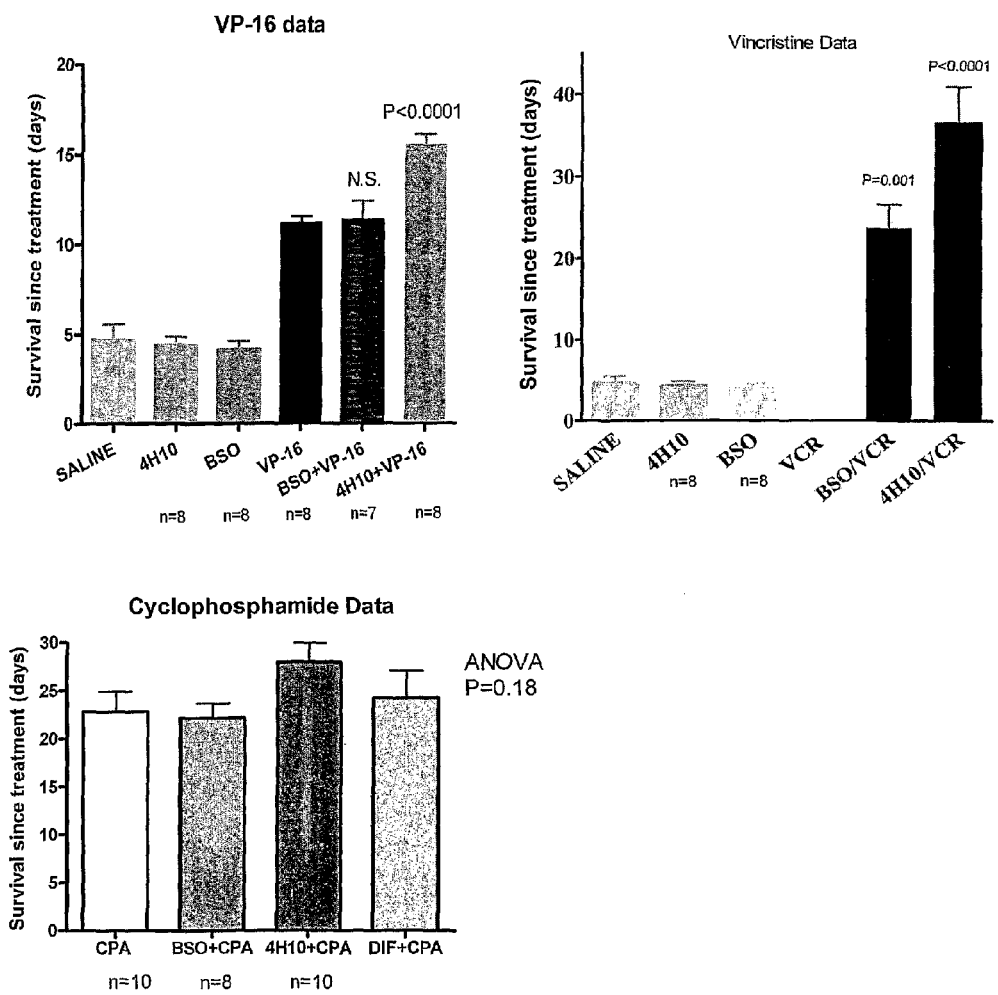
FIG. 20 contains plots showing in vivo efficacy of compound 4H10 in increasing the therapeutic effect of two known MRP1 substrate drugs, but not for a nonsubstrate drug.

FIG. 20 shows that compound 4H10 significantly increases the therapeutic effects of VP-16 and vincristine, which are two MRP1-transported chemotherapeutic agents. The therapeutic effects of cyclophosphamide, which is not transported by MRP1, was not increased. The test was a clinically relevant mouse model of NB that closely reflects the human disease (n=10, unless otherwise noted). FIG. 20 further shows the 4H10 is much more effective than BSO, a compound that inhibits MRP1 function by depleting the cellular glutathione pools required for MRP1 transport function (8, 9, 26, 27).

REFERENCES

1. R. V. Kondratov et al., *Proc Natl Acad Sci USA*, 98:14078-14083, 2001.
2. P. A. Pizzo et al., Principles and Practice of Pediatric Oncology, 1993, J. B. Lippincott Company: Philadelphia, p. 1350.
3. R. C. Seeger et al., *N Engl J* 313:1111-6, 1985.
4. N. Bown, *J Clin Path*, 54:897-910, 2001.
5. Castleberry, RP. Neuroblastoma. Eur J Cancer, 33:1430-7; discussion 1437-8, 1997.
6. L. Schweigerer et al., *Cancer Res*, 50:4411-6, 1990.
7. C. J. Thiele et al., *Nature*, 313:404-6, 1985.
8. W. A. Weiss et al., *EMBO J*, 16:2985-95, 1997.
9. M. D. Norris et al., *Med Ped Oncol*, 35:585-589, 2000.
10. E. M. Blackwood et al., *Science*, 251:1211-7, 1991.
11. C. Queva et al., *Oncogene*, 16:967-77, 1998.
12. T. K. Blackwell et al., *Science*, 250:1149-51, 1990.
13. K. Boon et al., *EMBO Journal*, 20:1383-93, 2001.
14. C. Grandori et al., *Sciences*, 22:177-81, 1997.
15. G. L. Scheffer et al., *Novartis Found Symp*, 243:19-31, 2002.
16. P. Borst et al., *J Natl Cancer Inst*, 92:1295-1302, 2000.
17. M. D. Norris et al., *New Engl J Med*, 334:231-8, 1996.
18. E. Teodori et al., *Farmaco*, 57:385-415, 2002.
19. H. L. Tai, *Current Opinion in Molecular Therapeutics*, 2:459-67, 2000.
20. A. H. Dantzig et al., *Curr Med Chem*, 8:39-50, 2001.
21. R. L. Shepard et al., *Int J Cancer*, 103:121-5, 2003.
22. D. R. Hipfner et al., *Biochim Biophys Acta*, 6:359-76, 1999.
23. Z. A. Chen et al., *Int J Cancer*, 93:107-113, 2001.
24. E. Schneider et al., *Cancer Res*, 54:152-8, 1994.
25. G. D. Leonard et al., *Curr Opin Investig Drugs*, 3: 1652-1659.
26. C. Burkhart et al., *Journal of the National Cancer Institute*, 95, 1394-1403 (2003).
27. P. J. Houghton et al., *Clin. Cancer Res.*, 8:3646-57 (2002).

What is claimed is:

1. A method of potentiating the activity of a chemotherapeutic drug in a cell or tissue expressing a multidrug transporter of the MRP family of transporters, comprising contacting the cell or tissue having the chemotherapeutic drug therein with a compound that inhibits an efflux capability of the multidrug transporter, wherein the compound is selected from the group consisting of

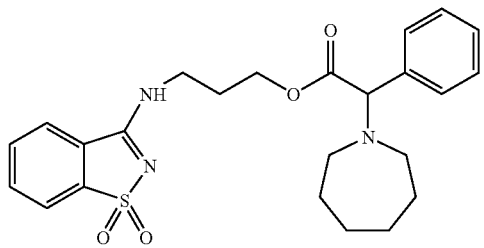

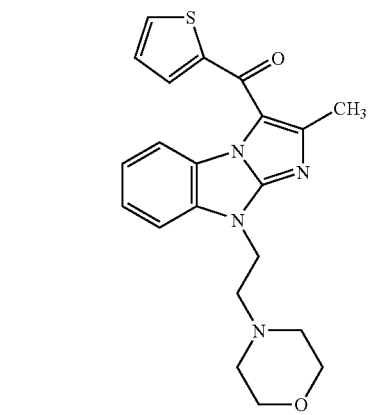

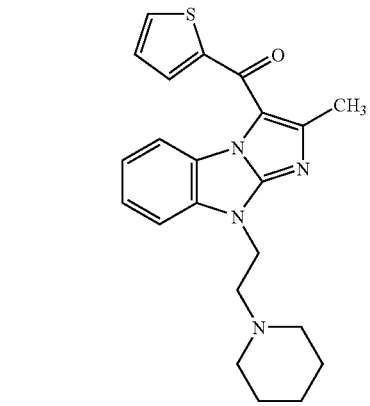

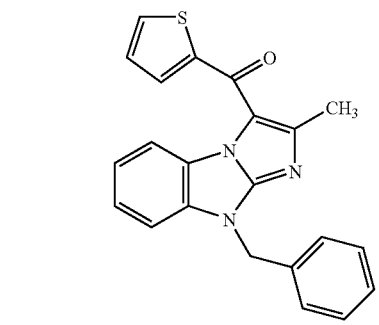

-continued

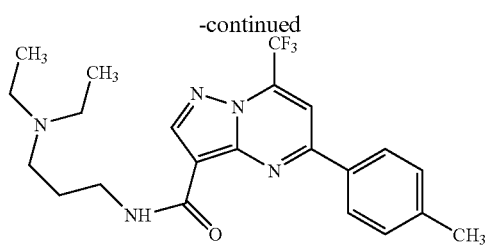

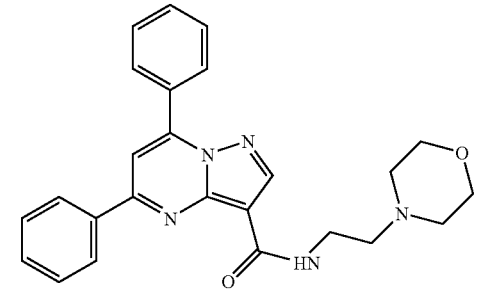

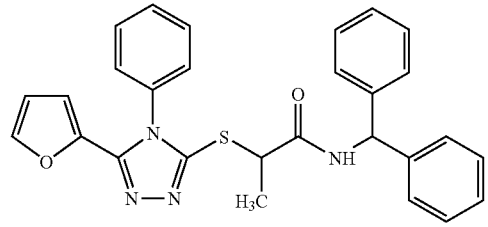

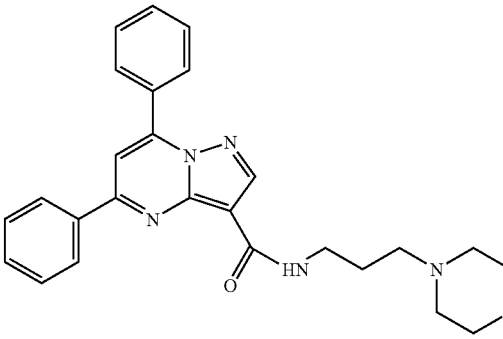

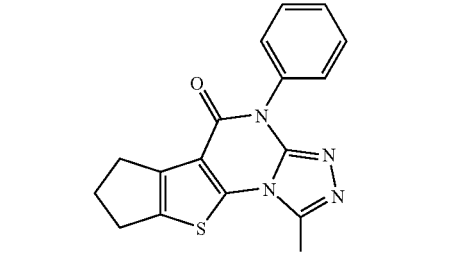

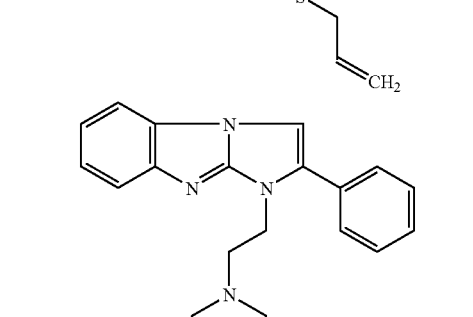

-continued

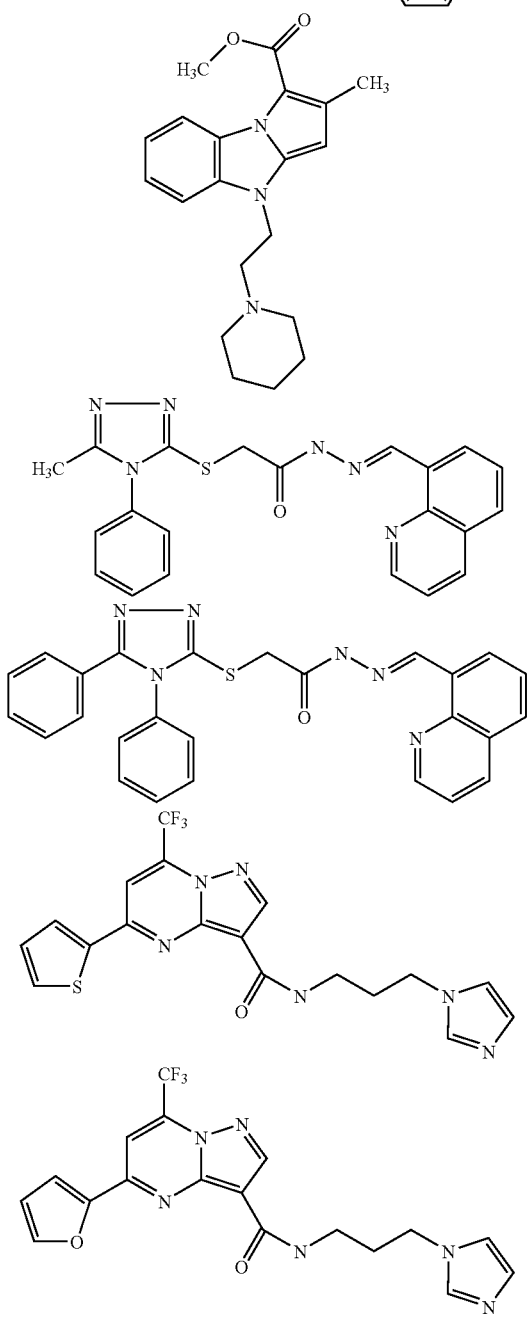

or a salt thereof, and mixtures thereof.

2. The method of claim 1 wherein the efflux capability of the multidrug transporter is selectively inhibited with respect to retaining the therapeutic drug in the cell or tissue, while maintaining normal efflux capabilities with respect to other compounds present in the cell or tissue.

3. The method of claim 1 wherein the MRP transporter is MRP1, MRP2, MRP3, or MRP4.

4. A method of treating a neuroblastoma, a renal cell carcinoma, or a colon cancer comprising administering to an individual in need thereof, (a) a therapeutically effective amount of a chemotherapeutic agent and (b) an effective amount of a compound that modulates the activity of a multidrug transporter, wherein the compound is selected from the group consisting of

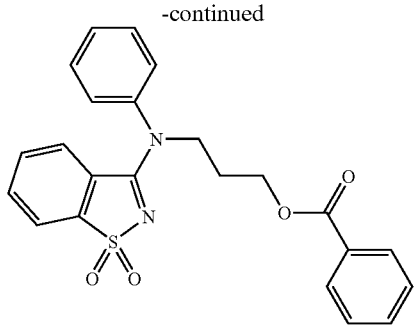

-continued
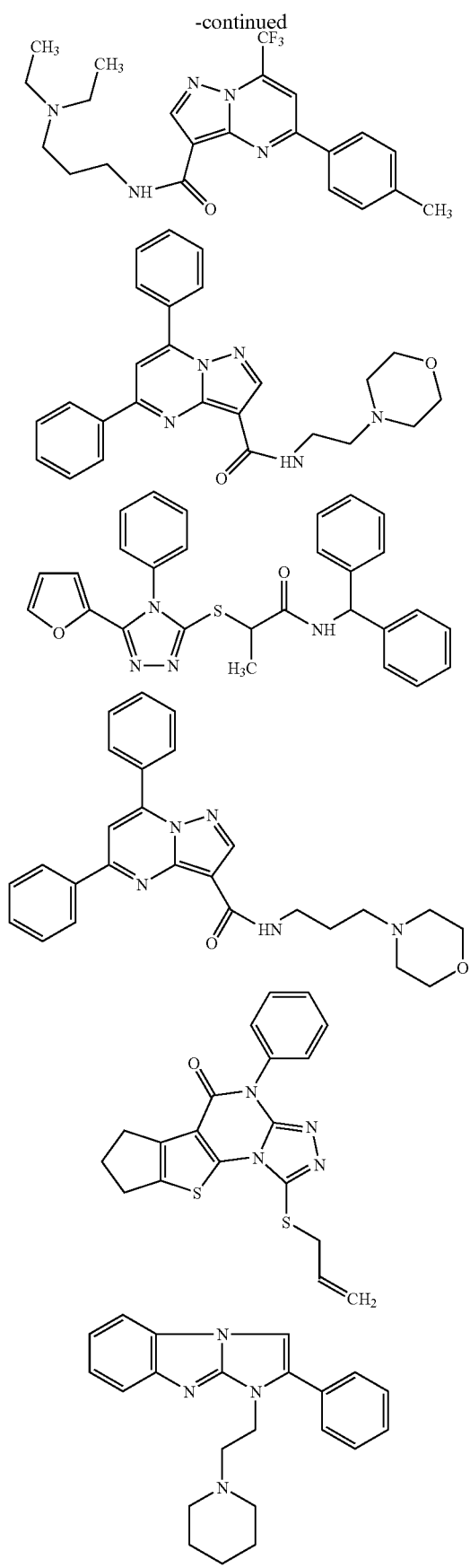
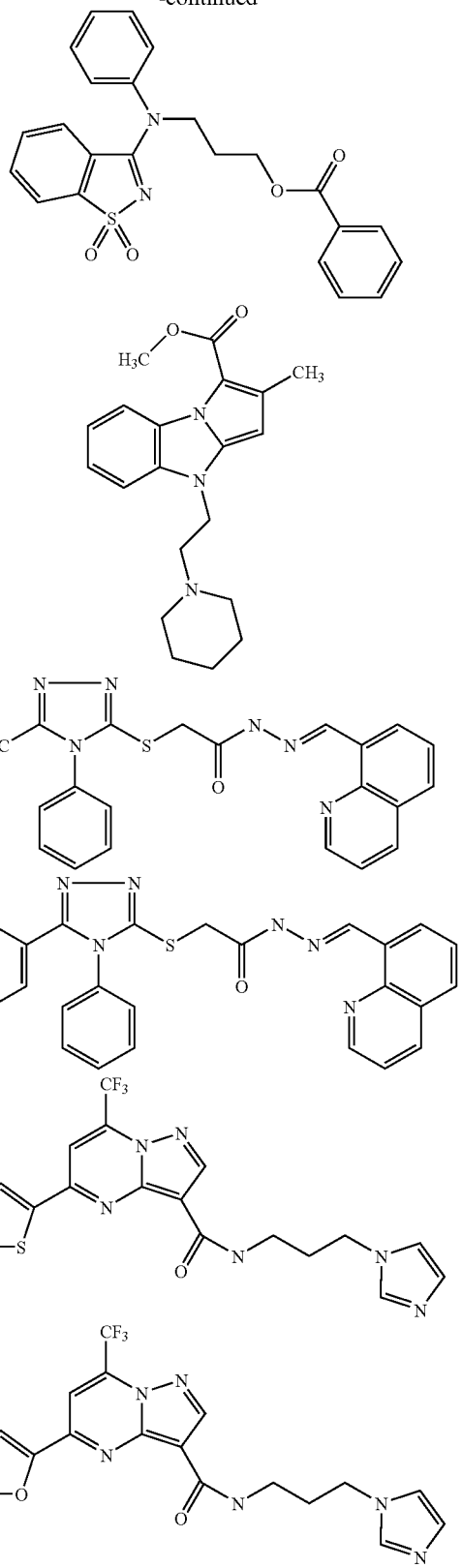
or a salt thereof, and mixtures thereof.
* * * * *

UNITED STATES PATENT AND TRADEMARK OFFICE
CERTIFICATE OF CORRECTION

PATENT NO. : 8,318,724 B2  Page 1 of 2
APPLICATION NO. : 11/579779
DATED : November 27, 2012
INVENTOR(S) : Gudkov et al.

It is certified that error appears in the above-identified patent and that said Letters Patent is hereby corrected as shown below:

In the Claims

Column 19, Lines 14-28, in Claim 1, delete " 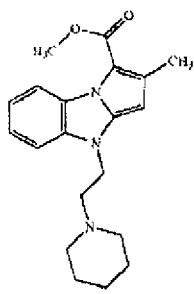 " and insert

-- 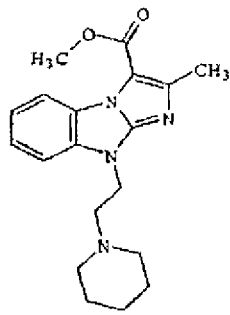 --, therefor.

Column 22, Lines 14-28, in Claim 4, delete " 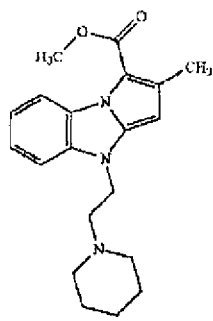 " and insert

Signed and Sealed this
Twenty-first Day of October, 2014

Michelle K. Lee
*Deputy Director of the United States Patent and Trademark Office*

CERTIFICATE OF CORRECTION (continued)
U.S. Pat. No. 8,318,724 B2

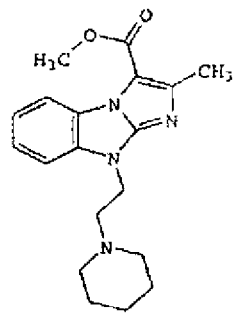

--                  --, therefor.